United States Patent
Dibbens et al.

(10) Patent No.: US 12,139,521 B2
(45) Date of Patent: Nov. 12, 2024

(54) DIAGNOSTIC AND THERAPEUTIC METHODS FOR EFMR (EPILEPSY AND MENTAL RETARDATION LIMITED TO FEMALES)

(71) Applicants: Central Adelaide Local Health Network Inc., Adelaide (AU); The University of Melbourne, Victoria (AU)

(72) Inventors: Leanne Michelle Dibbens, College Park (AU); Ingrid Eileen Scheffer, Victoria (AU); Samuel Frank Berkovic, Victoria (AU); John Charles Mulley, South Australia (AU); Jozef Gecz, South Australia (AU)

(73) Assignees: Central Adelaide Local Health Network Inc., Adelaide (AU); The University of Melbourne, Victoria (AU)

( * ) Notice: Subject to any disclaimer, the term of this patent is extended or adjusted under 35 U.S.C. 154(b) by 286 days.

(21) Appl. No.: 15/865,806

(22) Filed: Jan. 9, 2018

(65) Prior Publication Data
US 2018/0215803 A1   Aug. 2, 2018

Related U.S. Application Data

(62) Division of application No. 12/735,324, filed as application No. PCT/AU2009/000008 on Jan. 5, 2009, now Pat. No. 9,873,723.

(60) Provisional application No. 61/010,176, filed on Jan. 4, 2008.

(51) Int. Cl.
| | |
|---|---|
| C12Q 1/6883 | (2018.01) |
| A61K 48/00 | (2006.01) |
| C07K 14/705 | (2006.01) |
| C12Q 1/6876 | (2018.01) |
| G01N 33/566 | (2006.01) |
| A61K 38/00 | (2006.01) |

(52) U.S. Cl.
CPC .......... *C07K 14/705* (2013.01); *A61K 48/005* (2013.01); *C12Q 1/6883* (2013.01); *G01N 33/566* (2013.01); *A01K 2217/05* (2013.01); *A01K 2267/0356* (2013.01); *A61K 38/00* (2013.01); *C12Q 2600/136* (2013.01); *C12Q 2600/156* (2013.01); *C12Q 2600/158* (2013.01); *C12Q 2600/172* (2013.01); *G01N 2800/2857* (2013.01)

(58) Field of Classification Search
None
See application file for complete search history.

(56) References Cited

U.S. PATENT DOCUMENTS

| | | | |
|---|---|---|---|
| 6,582,908 B2 * | 6/2003 | Fodor | C12Q 3/00 506/30 |
| 6,881,537 B1 * | 4/2005 | Goudsmit | C12Q 1/6848 435/5 |
| 2004/0146890 A1 * | 7/2004 | Matsuzaki | C12Q 1/6883 435/287.2 |
| 2005/0026164 A1 * | 2/2005 | Zhou | C12Q 1/6888 506/17 |
| 2007/0243546 A1 * | 10/2007 | Cao | C12Q 1/6837 435/6.12 |
| 2008/0113351 A1 * | 5/2008 | Naito | A61P 5/26 536/23.1 |

FOREIGN PATENT DOCUMENTS

| | | | |
|---|---|---|---|
| WO | 2002/008322 | 11/2002 | |
| WO | WO 2002/088322 | 11/2002 | |
| WO | WO-02088322 A2 * | 11/2002 | ............ C07H 21/04 |
| WO | WO-2004036190 A2 * | 4/2004 | ............ C12Q 1/701 |
| WO | 2007/047796 | 4/2007 | |

OTHER PUBLICATIONS

Battaglia et al BioTechniques vol. 29, No. 1, 78-81 (Year: 2000).*
Bakalova et al J. Am. Chem. Soc. 9 vol. 127, 11328-11335 (Year: 2005).*
Hilario (Molecular Biotechnology,28, 77-80 (Year: 2004).*
Dibbens et al. 2008 Nature Genetics 40(6): 776-81.
Depienne et al. (2009 PLoS Genetics 5(2): e1000381.
Depienne & LeGuern 2012, Human Mutation 33, 627-634.
Depienne et al Human mutations, 2010, 32: E1959-E1975.
Irvine et al Clin Exp Dermatol. Jan. 2001;26(1):59-71, abstract only.
Mummidi et al( The Journal of Biological Chemistry, 2000, 275, 18946-18961.
Brookes et al Trends in Molecular Medicine, 2001, 512-516.
Kroese et al Genetics in Medicine, 2004, 475-480).
Ionnidis Plost Med, 2005, 2(8):124.
Hattersley et al (Lancet, 2005, 366, p. 1315-1323.
Hegele Arterioscler. Thromb. Vasc. Biol. 2002; 22; 1058-1061.
Juppner et al; Bone, vol. 17; 1995, pp. 39S-40S.
NCBI Sequence AI355593; last update: Jul. 9, 2007 (See Sequence).

(Continued)

*Primary Examiner* — Anoop K Singh
(74) *Attorney, Agent, or Firm* — Hoffmann & Baron, LLP

(57) ABSTRACT

Methods and kits for the diagnosis of illnesses related to protocadherin 19 (PCDH19) protein deficiency or altered PCDH19 protein function are provided, as well as methods and kits for the identification of a predisposition to such illnesses and methods of screening subjects to identify carriers of such illnesses and methods and kits for the therapeutic or prophylactic treatment of PCDH19 deficiency or altered PCDH19 protein function. Further, nucleotide and amino acid sequences corresponding to a complete PCDH19 open reading frame (ORF), mutant sequences encoding non-functional PCDH19 mRNA or altered PCDH19 mRNA are described along with transformed cells and non-human transgenic animals comprising wild-type or mutant PCDH19 ORF nucleotide sequences.

4 Claims, 5 Drawing Sheets

Specification includes a Sequence Listing.

(56) References Cited

OTHER PUBLICATIONS

Accession No. Q8TAB3 (See Sequence).
NCBI Sequence NP_001098715 (See Sequence).
NCBI Sequence XP_228429 (See Sequence).
Accession No. Q80TF3; Last update Mar. 3, 2009 (See Sequence).
NCBI Sequence AK122392.1 (See Sequence).
Ryan, et al., Nature Genetics (1997) 17;92-95.
Scheffer, et al., Brain (2008), 131, 918-927.
Dibbens, et al., Nature Genetics (2008) 40:6; 776-781.
Wolverton, et al., Genomics (2001) 73(1-3): 66-71.
Okazaki, DNA Research (2003) 10, 35-48.

\* cited by examiner

DIAGNOSTIC AND THERAPEUTIC METHODS FOR EFMR (EPILEPSY AND MENTAL RETARDATION LIMITED TO FEMALES)

CROSS REFERENCE TO RELATED APPLICATIONS

The present application is a Continuation of co-pending U.S. application Ser. No. 12/735,324, filed Jan. 31, 2011, which in turn claims priority from PCT Application No. PCT/AU2009/000008, filed Jan. 5, 2009, which in turn claims priority from U.S. Provisional Application Ser. No. 61/010,176, filed Jan. 4, 2008. Applicants claim the benefits of 35 U.S.C. § 120 and 35 U.S.C. § 365 as to the PCT application, and 35 U.S.C. § 119(e) as to the U.S. Provisional Application Ser. No. 61/010,176, and the entire disclosures of both applications are incorporated herein by reference in their entireties.

FIELD OF THE INVENTION

The present invention relates to nucleotide and amino acid sequences corresponding to a complete protocadherin 19 (PCDH19) open reading frame (ORF), and mutant nucleotide sequences encoding non-functional or altered PCDH19 mRNA or non-functional or altered PCDH19 protein which can result in illnesses related to PCDH19 protein deficiency or altered function in human subjects, in particular EFMR (Epilepsy and Mental Retardation limited to Females).

BACKGROUND OF THE INVENTION

Inherited diseases caused by mutations on the X chromosome are generally characterised by the affected status of carrier males and sparing of carrier females. EFMR (Epilepsy and Mental Retardation limited to Females) is a unique X-linked condition which, by contrast, spares carrier males and is expressed in females (Ryan S G et al., 1997). EFMR is a rare condition characterised by seizure onset in early childhood (6-36 months) and cognitive impairment. The phenotype is restricted to females with males apparently spared, demonstrating normal cognitive function and absence of seizures.

Prior to the studies described herein, the cause of EFMR was unknown, with the presence of EFMR not previously attributed to any specific genetic factor. The studies described herein now identify the protocadherin 19 (PCDH19) gene as responsible for EFMR.

By the systematic re-sequencing of 737 X-linked genes, seven different mutations in the PCDH19 gene were identified in seven unrelated families with EFMR. Five of these mutations result in the introduction of a premature termination codon resulting in non-functional PCDH19 mRNA that is degraded by nonsense mediated decay (NMD) processes. The two other mutations have been determined to be missense mutations and are likely to affect adhesiveness of the PCDH19 protein through impaired calcium binding.

PCDH19 is the first cadherin to be implicated in epilepsy and mental retardation. The expression analysis described herein shows a role for PCDH19 in normal neuronal development. A mechanism of phenotype rescue that saves transmitting males (ie carrier males) from clinically expressing the disorder is suspected, through a related male-specific human gene, protocadherin 11Y (PCDH11Y) (Blanco P et al., 2000). This mechanism is consistent with the remarkable mode of inheritance observed in EFMR.

The studies described herein have identified nucleotide and amino acid sequences corresponding to a complete PCDH19 open reading frame (ORF) as well as mutant sequences encoding non-functional PCDH19 mRNA or non-functional PCDH19 protein. These are shown to be related to illnesses associated with PCDH19 protein deficiency or altered function such as epilepsy and mental retardation, in particular EFMR. Further, male carriers of the PCDH19 deficient genotype have been shown to be rescued from the disease phenotype by the male-specific protocadherin PCDH11Y.

The identification of the complete PCDH19 ORF and the identification of mutations in the nucleotide sequence causing a disease state provide for methods for diagnosis of illnesses related to PCDH19 protein deficiency or altered PCDH19 protein function, methods for the identification of a predisposition to such illnesses, methods of screening to identify carriers of such illnesses methods, and agents for the therapeutic or prophylactic treatment of PCDH19 deficiency.

SUMMARY OF THE INVENTION

Thus, in a first aspect, the present invention provides a method of diagnosing an illness related to functional protocadherin 19 (PCDH19) protein deficiency or altered PCDH19 protein function, or assessing a predisposition to an illness related to functional PCDH19 protein deficiency or altered PCDH19 protein function, or screening to identify carriers of illnesses related to functional PCDH19 protein deficiency or altered PCDH19 protein function, wherein said method comprises the step of:
  (i) detecting in a suitable biological sample from a subject, a loss of PCDH19 protein function or altered PCDH19 protein function.

In a second aspect, the invention provides a kit for diagnosing an illness related to functional protocadherin 19 (PCDH19) protein deficiency or altered PCDH19 protein function, or assessing a predisposition to an illness related to functional PCDH19 protein deficiency or altered PCDH19 protein function, or screening to identify carriers of illnesses related to functional PCDH19 protein deficiency or altered PCDH19 protein function, wherein said kit comprises one or more of the following: an antibody or fragment thereof which specifically binds to PCDH19 protein or polypeptide, or a fragment or variant thereof; and an oligonucleotide probe/primer molecule which specifically hybridises to a polynucleotide molecule encoding PCDH19 protein or polypeptide, or a fragment or variant thereof under high stringency conditions.

In a third aspect, the present invention provides for the use of: a polynucleotide molecule comprising a nucleotide sequence showing at least 70% sequence identity to a complete protocadherin 19 (PCDH19) open reading frame (ORF) nucleotide sequence according to SEQ ID NO: 1, wherein said nucleotide sequence encodes a functional PCDH19 protein or polypeptide, or functional fragment or functional variant thereof encoded by a polynucleotide molecule comprising a nucleotide sequence showing at least 70% sequence identity to the complete PCDH19 ORF nucleotide sequence according to SEQ ID NO: 1; in the treatment of PCDH19 protein deficiency or altered PCDH19 protein function in a subject.

In a fourth aspect, the present invention provides a method for the therapeutic or prophylactic treatment of protocadherin 19 (PCDH19) protein deficiency or altered PCDH19 protein function in a subject, wherein said method comprises the step of:
(i) administering to said subject: a polynucleotide molecule comprising a nucleotide sequence showing at least 70% sequence identity to the complete protocadherin 19 (PCDH19) open reading frame (ORF) nucleotide sequence according to SEQ ID NO: 1, wherein said nucleotide sequence encodes a functional PCDH19 protein or polypeptide, or a functional fragment or functional variant thereof; a functional PCDH19 protein or polypeptide, or functional fragment or functional variant thereof encoded by a polynucleotide molecule comprising a nucleotide sequence showing at least 70% sequence identity to the complete PCDH19 ORF nucleotide sequence according to SEQ ID NO: 1; and/or an agent that compensates for the loss of PCDH19 protein function; optionally in combination with a pharmaceutically-acceptable carrier.

In a fifth aspect, the present invention provides an agent capable of treating a deficiency in functional protocadherin 19 (PCDH19) protein or altered PCDH19 protein function in a subject.

In a sixth aspect, the present invention provides a method for identifying an agent capable of treating a deficiency in functional protocadherin 19 (PCDH19) protein or altered PCDH19 protein function, wherein said method comprises the steps of;
(i) providing a cell or animal comprising a polynucleotide molecule comprising a mutant sequence of the PCDH19 ORF nucleotide sequence shown as SEQ ID NO: 1;
(ii) contacting a test agent with said cell or administering a test agent to said animal; and
(iii) comparing a response in said cell or animal with a control response.

In a seventh aspect, the present invention provides a kit for use in the method of the sixth aspect, wherein said kit comprises instructions for the operation of the method together with one or more containers and/or vessels containing one or more cell(s) or animal(s) comprising a polynucleotide molecule comprising a mutant sequence of the protocadherin 19 (PCDH19) ORF nucleotide sequence shown as SEQ ID NO: 1.

In an eighth aspect, the present invention provides a kit for identifying an agent capable of treating a deficiency in functional protocadherin 19 (PCDH19) protein or altered PCDH19 protein function, wherein said kit comprises;
(i) a cell or animal comprising a polynucleotide molecule comprising a mutant sequence of the PCDH19 ORF nucleotide sequence shown as SEQ ID NO: 1; and optionally,
(ii) a control cell or animal comprising a polynucleotide molecule comprising a wild-type form of the complete PCDH19 ORF nucleotide sequence shown as SEQ ID NO: 1, said wild-type form encoding a functional PCDH19 protein or polypeptide, or a functional fragment or functional variant thereof.

In a ninth aspect, the present invention provides an isolated protein or polypeptide comprising an amino acid sequence encoded by a nucleotide sequence showing at least 70% sequence identity to a complete protocadherin 19 (PCDH19) ORF nucleotide sequence according to SEQ ID NO: 1, or a functional fragment or variant thereof.

In a tenth aspect, the present invention provides an isolated polynucleotide molecule comprising a nucleotide sequence showing at least 70% sequence identity to a complete protocadherin 19 (PCDH19) ORF nucleotide sequence according to SEQ ID NO: 1 or a complementary sequence thereto.

In an eleventh aspect, the present invention provides a cell transformed with the polynucleotide molecule of the tenth aspect.

In a twelfth aspect, the present invention provides a non-human animal comprising the polynucleotide molecule of the tenth aspect.

DETAILED DESCRIPTION OF THE INVENTION

Figure 1:
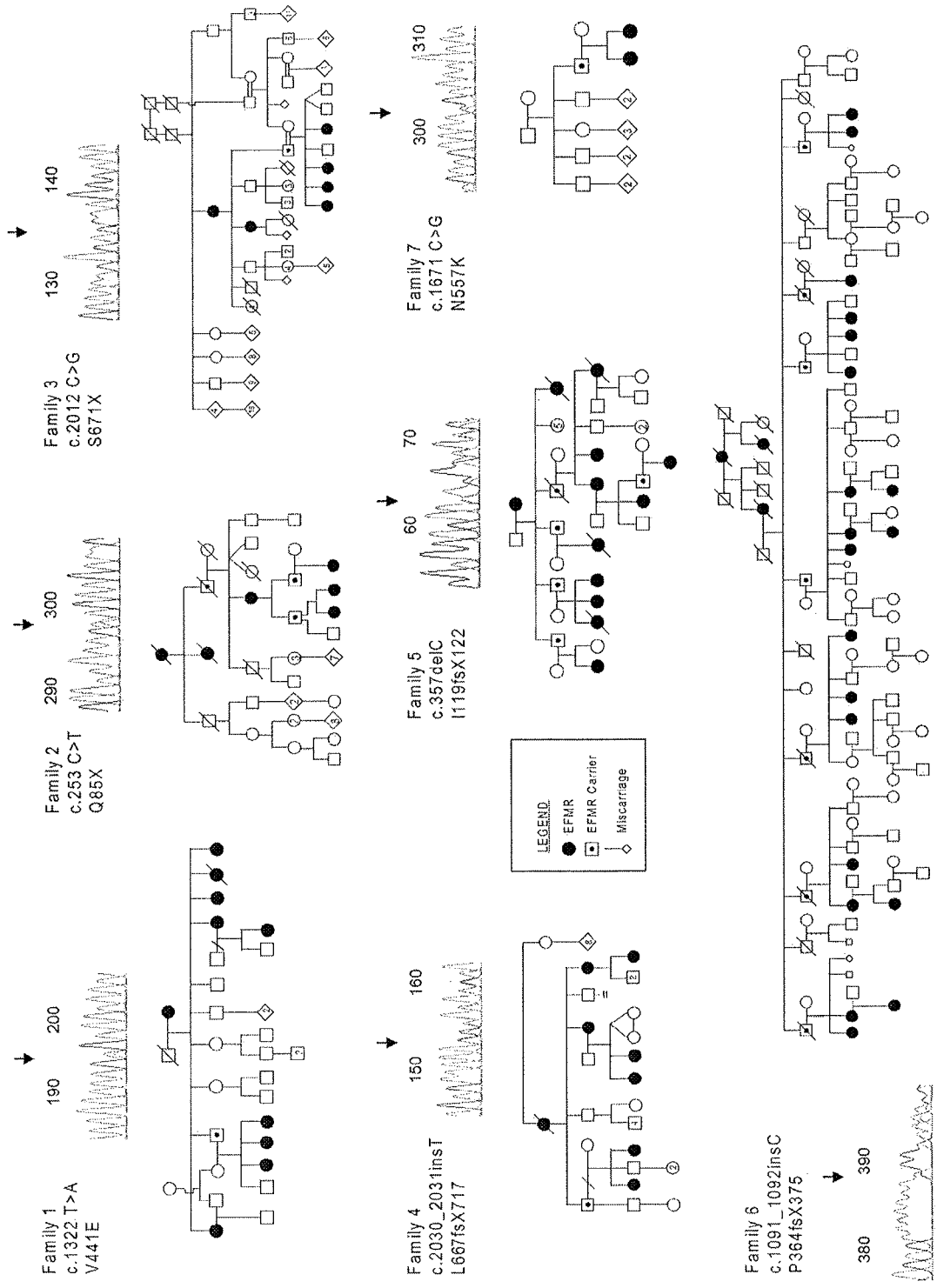
FIG. 1 shows pedigrees of the seven EFMR families assessed in the studies described herein. A specific mutation in the PCDH19 gene, responsible for EFMR in each family, is indicated alongside the corresponding sequence chromatogram section showing the location of the mutation. Females presenting with EFMR are represented by filled circles and carrier males are represented by small circles within squares.

The present invention generally relates to methods and kits for the diagnosis of illnesses related to PCDH19 protein deficiency or altered PCDH19 protein function, methods and kits for the identification of a predisposition to such illnesses, methods of screening subjects to identify carriers of such illnesses, and methods and kits for the therapeutic or prophylactic treatment of PCDH19 deficiency or altered PCDH19 protein function. The present invention also relates to nucleotide and amino acid sequences corresponding to a complete PCDH19 ORF, mutant sequences encoding non-functional PCDH19 mRNA (eg which may be degraded by nonsense mediated mRNA degradation (NMD) processes) or altered PCDH19 mRNA, or non-functional PCDH19 protein or altered PCDH19 protein causative of illnesses related to PCDH19 protein deficiency or altered function in human subjects, and transformed cells and transgenic non-human animals comprising wild-type or mutant PCDH19 ORF nucleotide sequences.

Thus, in a first aspect, the present invention provides a method of diagnosing an illness related to functional protocadherin 19 (PCDH19) protein deficiency or altered PCDH19 protein function, or assessing a predisposition to an illness related to functional PCDH19 protein deficiency or altered PCDH19 protein function, or screening to identify carriers of illnesses related to functional PCDH19 protein deficiency or altered PCDH19 protein function, wherein said method comprises the step of:

(i) detecting in a suitable biological sample from a subject, a loss of PCDH19 protein function or altered PCDH19 protein function.

Illnesses resulting from PCDH19 deficiency or altered PCDH19 protein function include epilepsy and/or mental retardation, in particular EFMR. Thus, preferably, the method of the first aspect provides a method of diagnosing EFMR, assessing a predisposition to EFMR or screening carriers of EFMR, in particular, male carriers of EFMR. In particular, preferred methods include prenatal diagnosis or screeing of EFMR.

The detection of a loss of PCDH19 protein function or altered PCDH19 protein function can be used, in the case of a subject for which EFMR has not previously been diagnosed, either on its own or in combination with other tests, to diagnose EFMR in the subject. For a subject in which EFMR has not previously been diagnosed and who is not showing any signs of ill health due to EFMR, the detection of a loss of PCDH19 protein function or altered PCDH19 protein function, can be used in an assessment of a predisposition to EFMR or carrier status of EFMR.

The detection of a loss of PCDH19 protein function or altered PCDH19 protein function can involve one or more of detecting a mutant sequence in a PCDH19 ORF of the subject which encodes non-functional or altered PCDH19 mRNA or non-functional or altered PCDH19 protein (eg by genotyping the subject) or causes reduced expression of PCDH19 protein (eg mutations of the PCDH19 gene expression control sequences). Conveniently, this may be achieved by amplifying the PCDH19 nucleotide sequences (or a target region thereof) within a suitable biological sample and, thereafter sequencing the amplication product. Preferably, the detection of a loss of PCDH19 protein function involves detecting a mutant sequence in the extracellular (EC) domain-encoding region of a PCDH19 ORF of the subject such as, for example, a mutant sequence causing an amino acid substitution within or adjacent to a calcium ion-binding site (eg within 20 amino acids of a calcium ion-binding site) such that calcium ion binding is impaired, or a mutant sequence comprising a premature termination codon (PTC).

The detection of a loss of PCDH19 protein function or altered PCDH19 protein function may also be indirectly achieved by conducting, for example, assays for functional PCDH19 protein or polypeptide. Assays for detecting functional PCDH19 protein or polypeptide, preferably comprise the use of an antibody or fragment thereof that is capable of specifically binding with PCDH19 protein or polypeptide, or a functional fragment or functional variant thereof, to determine the relative amount of the protein or polypeptide that is present in a suitable biological sample taken from the subject. This can involve the use of any of the methods well known to persons skilled in the art (eg standard ELISA-based methods or in situ immunofluorescence using tissue section samples). As such, the relative amount of functional PCDH19 protein or polypeptide can be determined by quantitatively detecting the protein or polypeptide with a specific antibody or fragment thereof (ie a primary antibody) which is either directly conjugated to a detectable label or is otherwise detected via a secondary antibody or fragment thereof directly conjugated to a detectable label. Suitable detectable labels include chromophores, fluorophores (eg fluorescein or FITC), radiolabels (eg $^{125}$I), and enzymes such as horseradish peroxidase. These labels can be used in methods and systems as are well known to persons skilled in the art, which provide for the automation or partial automation of the step of detecting the functional PCDH19 protein or polypeptide (eg by a microplate reader or use of a flow cytometer). Generally, the relative amount of functional PCDH19 protein will be determined by comparison against the amount, or range of amounts, present in "normal samples" (eg samples from equivalent biological samples taken from normal subject(s)).

Functional PCDH19 protein or polypeptide may be characterised as being encoded by a nucleotide sequence showing at least 70% sequence identity, preferably at least 85% sequence identity, and, more preferably, at least 95% sequence identity to a complete PCDH19 open reading frame (ORF) nucleotide sequence according to:

(SEQ ID NO: 1)

```
atggagtcgc tcctgctgcc ggtgctgctg ctgctggcca tactgtggac gcaggctgcc    60
gccctcatta atctcaagta ctcggtagaa gaggagcagc gcgccgggac ggtgattgcc   120
aacgtggcca aagacgcgcg agaggcgggc ttcgcgctgg accccggca ggcttcagcc   180
```

-continued

```
tttcgcgtgg tgtccaactc ggctccacac ctagtggaca tcaatcccag ctctggcctg    240
ctggtcacca agcagaagat tgaccgtgat ctgctgtgcc gccagagccc caagtgcatc    300
atctcgctcg aggtcatgtc cagctcaatg gaaatctgcg tgataaaggt ggagatcaag    360
gacctgaacg acaatgcgcc cagtttcccg gcagcacaga tcgagctgga gatctcggag    420
gcagccagcc ctggcacgcg catcccgctg acagcgctt acgatccaga ctcaggaagc    480
tttggcgtgc agacttacga gctcacgccc aacgagctgt tcggcctgga gatcaagacg    540
cgcggcgacg gctcccgctt tgccgaactc gtggtggaaa agagcctgga ccgcgagacg    600
cagtcgcact acagcttccg aatcactgcg ctagacggtg gcgacccgcc gcgcctgggc    660
accgttggcc ttagtatcaa ggtgaccgac tccaatgaca caacccggt gtttagcgag    720 tccacctacg cggtgagcgt gccagaaaac tcgcctccca acacacccgt catccgcctc    780
aacgccagcg atccagacga gggcaccaac ggccaggtgg tctactcctt ctatggctac    840
gtcaacgacc gcacgcgcga gctctttcag atcgacccgc acagtggcct ggtcactgtc    900
actggcgctt tagactacga agaggggcac gtgtacgaac tggacgtgca ggctaaggac    960
ttggggccca attccatccc ggcacactgc aaggtcaccg tcagcgtgct ggacaccaat   1020
gacaatccgc cggtcatcaa cctgctgtca gtcaacagtg agcttgtgga ggtcagcgag   1080 agcgccccc cgggctacgt gatcgccttg gtgcgggtgt ctgatcgcga ctcaggcctc   1140
aatggacgtg tgcagtgccg tttgctgggc aatgtgccct tcgactgca ggaatatgag   1200 agcttctcca ctattctggt ggacggacg ctggaccgcg agcagcacga ccaatacaac   1260
ctcacaattc aggcacgcga cggcggcgtg cccatgctgc agagtgccaa gtcctttacc   1320
gtgctcatca ctgacgaaaa tgacaaccac ccgcactttt ccaagcccta ctaccaggtc   1380
attgtgcagg agaacaacac gcctggcgcc tatctgctct ctgtgtctgc tcgcgacccc   1440
gacctgggtc tcaacggcag tgtctcctac cagatcgtgc cgtcgcaggt gcgggacatg   1500
cctgtcttca cctatgtctc catcaatccc aactcaggcg acatctacgc gctgcgatcc   1560
tttaaccacg agcagaccaa ggcgttcgaa ttcaaggtgc tggccaagga cggcggcctt   1620
ccctcactgc aaagcaacgc tacggtgcgg gtcatcatcc tcgacgtcaa cgacaacacc   1680
ccggtcatca cagccccacc tctgattaac ggcactgccg aggtctacat accccgcaac   1740
tctggcatag gctacctggt gactgttgtc aaggcagaag actacgatga gggcgaaaat   1800
ggccgagtca cctacgacat gaccgagggc gaccgcggct tctttgaaat agaccaggtc   1860
aatggcgaag tcagaaccac ccgcaccttc ggggagagct ccaagtcctc ctatgagctt   1920
atcgtggtgg ctcacgacca cggcaagaca tctctctctg cctctgctct cgtcctaatc   1980
tacttgtccc ctgctctcga tgcccaagag tcaatgggcc ctgtgaactt gtccttgatt   2040
ttcattattg ccctgggctc cattgcgggc atcctctttg taactatgat cttcgtggca   2100
atcaagtgca agcgagacaa caaagagatc cggacctaca actgcagtaa ttgtttaacc   2160
atcacttgtc tcctcggctg ttttataaaa ggacaaaaca gcaagtgtct gcattgcatc   2220
tcggtttctc ccattagcga ggagcaagac aaaaagacag aggagaaagt gagcctaagg   2280
ggaaagagaa ttgctgagta ctcctatggg catcaaaaga aatcaagcaa gaagaaaaaa   2340
atcagtaaga atgacatccg cctggtaccc cgggatgtgg aggagacaga caagatgaac   2400
gttgtcagtt gctcttccct gacctcctcc ctcaactatt ttgactacca ccagcagacg   2460 ctgccctgg gctgccgccg ctctgagagc actttcctga atgtggagaa ccagaatacc   2520
cgcaacacca gtgctaacca catctaccat cactctttca acagccaggg gccccagcag   2580
```

-continued

```
cctgacctga ttatcaacgg tgtgcctctg cctgagactg aaaactattc ttttgactcc 2640
aactacgtga atagccgagc ccatttaatc aagagcagct ccaccttcaa ggacttagag 2700
ggcaacagcc tgaaggatag tggacatgag gagagtgacc aaactgacag tgagcatgat 2760
gtccagcgga gcctgtattg tgatactgct gtcaacgatg tgctgaacac cagtgtgacc 2820
tccatgggat ctcagatgcc tgatcatgat cagaatgaag gatttcattg ccgggaagaa 2880
tgccggattc ttggccactc tgacaggtgc tggatgcccc ggaacccat gcccatccgt 2940 tccaagtccc ctgagcatgt gaggaacatc atcgcgctgt ctattgaagc tactgctgct 3000
gatgtcgagg cttatgacga ctgcggcccc accaaacgga cttttcgcaac ctttgggaaa 3060 gatgtcagcg accacccggc tgaggagagg cctaccctga aaggcaagag gactgtcgat 3120
gtgaccatct gcagcccaa ggtcaacagc gttatccggg aggcaggcaa tggctgtgag 3180
gcgattagcc ctgtcacctc cccctccac ctcaagagct ctctgcccac caagccttcc 3240
gtgtcttaca ccattgccct ggctccccca gcccgtgatc tggagcagta tgtcaacaat 3300
gtcaacaatg gccctactcg tccctctgaa gctgagcccc gtggagctga tagcgagaaa 3360
gtcatgcatg aggtcagccc cattctgaag gaaggtcgca acaaagagtc ccctggtgtg 3420
aagcgtctga aggatatcgt tctctaa.                                    3447
```

Most preferably, functional PCDH19 protein or polypeptide is characterised by comprising an amino acid sequence according to:

On the other hand, assays for detecting loss of PCDH19 protein function may comprise the use of an antibody or fragment thereof that is capable of distinguishing between,

```
                                                        (SEQ ID NO: 2)
MESLLLPVLLLLAILWTQAAALINLKYSVEEEQRAGTVIANVAKDAREAGFALDPRQASA    60

FRVVSNSAPHLVDINPSSGLLVTKQKIDRDLLCRQSPKCIISLEVMSSSMEICVIKVEIK   120

DLNDNAPSFPAAQIELEISEAASPGTRIPLDSAYDPDSGSFGVQTYELTPNELFGLEIKT   180

RGDGSRFAELVVEKSLDRETQSHYSFRITALDGGDPPRLGTVGLSIKVTDSNDNNPVFSE   240

STYAVSVPENSPPNTPVIRLNASDPDEGTNGQVVYSFYGYVNDRTRELFQIDPHSGLVTV   300

TGALDYEEGHVYELDVQAKDLGPNSIPAHCKVTVSVLDTNDNPPVINLLSVNSELVEVSE   360

SAPPGYVIALVRVSDRDSGLNGRVQCRLLGNVPFRLQEYESFSTILVDGRLDREQHDQYN   420

LTIQARDGGVPMLQSAKSFTVLITDENDNHPHFSKPYYQVIVQENNTPGAYLLSVSARDP   480

DLGLNGSVSYQIVPSQVRDMPVFTYVSINPNSGDIYALRSFNHEQTKAFEFKVLAKDGGL   540

PSLQSNATVRVIILDVNDNTPVITAPPLINGTAEVYIPRNSGIGYLVIVVKAEDYDEGEN   600

GRVTYDMTEGDRGFFEIDQVNGEVRTTRIFGESSKSSYELIVVAHDHGKTSLSASALVLI   660

YLSPALDAQESMGSVNLSLIFIIALGSIAGILFVTMIFVAIKCKRDNKEIRTYNCSNCLT   720

ITCLLGCFIKGQNSKCLHCISVSPISEEQDKKTEEKVSLRGKRIAEYSYGHQKKSSKKKK   780

ISKNDIRLVPRDVEETDKMNVVSCSSLTSSLNYFDYHQQTLPLGCRRSESTFLNVENQNT   840

RNTSANHIYHHSFNSQGPQQPDLIINGVPLPETENYSFDSNYVNSRAHLIKSSSTFKDLE   900

GNSLKDSGHEESDQTDSEHDVQRSLYCDTAVNDVLNTSVTSMGSQMPDHDQNEGFHCREE   960

CRILGHSDRCWMPRNPMPIRSKSPEHVRNIIALSIEATAADVEAYDDCGPTKRTFATFGK  1020

DVSDHPAEERPTLKGKRTVDVTICSPKVNSVIREAGNGCEAISPVISPLHLKSSLPTKPS  1080

VSYTIALAPPARDLEQYVNNVNNGPTRPSEAEPRGADSEKVMHEVSPILKEGRNKESPGV  1140

KRLKDIVL.                                                     1148
``` for example, a wild-type PCDH19 protein or polypeptide and a non-functional variant thereof. This may or may not result in the identification of the particular form of the PCDH19 protein or polypeptide that is present in the biological sample taken from the subject.

Otherwise, assays for detecting loss of PCDH19 protein function may comprise determining the relative amount of messenger RNA (mRNA) encoding functional PCDH19 protein or polypeptide in a suitable biological sample taken from the subject. The relative amount of mRNA encoding the protein or polypeptide may be determined by any of the methods well known to persons skilled in the art including Northern blot (by comparison to reference samples) and PCR-based mRNA quantification methods (eg using RT-PCR with primers conjugated to a detectable label). Generally, the relative amount of mRNA encoding the protein or polypeptide will be determined by comparison against the amount, or range of amounts, present in "normal samples" (eg samples from equivalent biological samples taken from normal subject(s)).

Most preferably, the detection of a loss of PCDH19 protein function comprises detecting a mutant sequence encoding a non-functional variant of the PCDH19 amino acid sequence shown as SEQ ID NO: 2. Said mutant sequence may comprise any one or more of the nucleotide changes, relative to the nucleotide sequence shown as SEQ ID NO: 1, as follows: 1322 T>A, 253 C>T, 2012 C>G, 2030_2031insT, 1671 C>G, 357delC and 1091_1092insC. Methods for the detection of such nucleotide changes may comprise the step of detecting any hybridisation of a suitable oligonucleotide probe/primer molecule under high stringency conditions to the mutant sequence present in a suitable biological sample. High stringency conditions are well known to persons skilled in the art, and are typically characterised by high temperature (ie high annealing temperature) and low ionic strength (ie low salt concentration, especially of $MgCl_2$, KCl and NaCl). Thus, high stringency conditions may vary according to the circumstances of the hybridisation (ie for probe hybridisation, PCR amplification, etc). For the purposes of the present invention, the term "high stringency conditions" is to be understood as referring to such conditions applicable to probe hybridisation (eg conditions which: (1) employ low ionic strength and high temperature for washing, for example, 15 mM NaCl/1.5 mM sodium citrate/0.1% $NaDodSO_4$ at 50° C.; (2) employ, during hybridisation, a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (750 mM NaCl, 75 mM sodium citrate), 50 mM sodium phosphate (pH 6.8), 0.1% sodium pyrophosphate, 5×Denhardt's solution, sonicated salmon sperm DNA (50 μg/ml), 0.1% SDS and 10% dextran sulfate at 42° C. in 0.2×SSC (30 mM NaCl, 3 mM sodium citrate) and 0.1% SDS). An oligonucleotide molecule useful in the detection of a mutant sequence according to the present invention may be suitable for use as, for example, a probe or primer sequence. Typically, the oligonucleotide molecule will consist of 10 to 50 nucleotides and, more preferably, about 15 to 30 nucleotides. Preferably, the oligonucleotide molecule is derived from the nucleotide sequence shown as SEQ ID NO: 1 or a complementary sequence thereto, or the nucleotide sequence as shown as SEQ ID NO: 1 but incorporating one or more of the nucleotide changes mentioned above (ie 1322 T>A, 253 C>T, 2012 C>G, 2030_2031insT, 1671 C>G, 357delC and 1091_1092insC) or a complementary sequence thereto.

For the step of detecting a loss of PCDH19 protein function or altered PCDH19 protein function, a suitable biological sample taken from the subject may be selected from, for example, tissue biopsies and fixed sections (eg formalin fixed or paraffin embedded) or fixed cell samples prepared therefrom, including epithelial samples, smear samples, blood samples, faecal samples, urine samples or buccal samples. The sample may be pre-treated by, for example, filtration, separation or extraction methods to partly or completely purify or isolate cells, proteins, polypeptides, polynucleotide molecules, oligonucleotide molecules or fragments thereof or fractions containing these components.

In a second aspect, the invention provides a kit for diagnosing an illness related to functional PCDH19 protein deficiency or altered PCDH19 protein function, or assessing a predisposition to an illness related to functional PCDH19 protein deficiency or altered PCDH19 protein function, or screening to identify carriers of illnesses related to functional PCDH19 protein deficiency or altered PCDH19 protein function, wherein said kit comprises one or more of the following: an antibody or fragment thereof which specifically binds to PCDH19 protein or polypeptide, or a fragment or variant thereof; and an oligonucleotide probe/primer molecule which specifically hybridises to a polynucleotide molecule encoding PCDH19 protein or polypeptide, or a fragment or variant thereof under high stringency conditions.

Such kits may comprise, for example, instructions for the operation of the method and, optionally, for thereafter diagnosing an illness related to functional PCDH19 protein deficiency or altered PCDH19 protein function, or assessing a predisposition to an illness related to functional PCDH19 protein deficiency or altered PCDH19 protein function, or identifying carriers of illnesses related to functional PCDH19 protein deficiency or altered PCDH19 protein function, together with one or more containers or vessels containing said antibody or fragment thereof and/or said oligonucleotide probe/primer molecule.

Preferably, said antibody or fragment thereof will bind to a protein or polypeptide comprising an amino acid sequence showing at least 70% sequence identity to the PCDH19 amino acid sequence according to SEQ ID NO: 2. Further, preferably, said oligonucleotide probe/primer molecule will hybridise to a polynucleotide molecule comprising a nucleotide sequence showing at least 70% sequence identity to the complete PCDH19 ORF nucleotide sequence according to SEQ ID NO: 1.

In a third aspect, the present invention provides for the use of: a polynucleotide molecule comprising a nucleotide sequence showing at least 70% sequence identity to the complete protocadherin 19 (PCDH19) open reading frame (ORF) nucleotide sequence according to SEQ ID NO: 1, wherein said nucleotide sequence encodes a functional PCDH19 protein or polypeptide, or a functional fragment or functional variant thereof; or a functional PCDH19 protein or polypeptide, or functional fragment or functional variant thereof encoded by a polynucleotide molecule comprising a nucleotide sequence showing at least 70% sequence identity to the complete PCDH19 ORF nucleotide sequence according to SEQ ID NO: 1; in the treatment of PCDH19 protein deficiency or altered PCDH19 protein function in a subject.

Preferably, the said nucleotide sequence shows at least 85% sequence identity, and, more preferably, at least 95% sequence identity to the complete PCDH19 ORF nucleotide sequence according to SEQ ID NO: 1.

Most preferably, the said functional PCDH19 protein or polypeptide comprises an amino acid sequence according to SEQ ID NO: 2.

For the sake of clarity, percentage levels of nucleotide sequence identity and amino acid sequence identity referred to herein are to be understood as meaning the "match percentage" calculated by the EMBL-EBI Multiple Alignment Using Fast Fourier Transform (MAFFT) tool using the Blosum 62 matrix (http://www.ebi.ac.uk/mafft/) and standard default settings.

The term "functional fragment" as used herein is to be understood as referring to a fragment which exhibits biological activity that is substantially equivalent to a protein or polypeptide comprising the complete PCDH19 amino acid sequence shown as SEQ ID NO: 2.

The term "variant" as used herein in relation to an amino acid sequence, is to be understood as referring to a protein or polypeptide, or fragment thereof, comprising an amino acid sequence showing a high level of sequence identity to the corresponding complete (or part thereof as the case may be) of the amino acid sequence shown as SEQ ID NO: 2, but which includes one or more variations in the sequence which do not result in any significant alteration of the biological activity of its derivative protein or polypeptide (ie a protein or polypeptide comprising the complete PCDH19 amino acid sequence shown as SEQ ID NO: 2) or which otherwise results in enhanced or reduced biological activity (eg variants may include one or more amino acid substitutions, additions or deletions, or may include the addition or deletion of a sequence of amino acids, which enhances or reduces biological activity). A variant with enhanced or reduced biological activity can therefore be regarded as a "functional variant", whereas a variant which has no or minimal biological activity can be regarded as a "non-functional variant". Variations that do not result in any significant alteration of the biological activity may include conservative amino acid substitutions. Exemplary conservative amino acid substitutions are provided in Table 1 below. Particular conservative amino acids envisaged are: G, A, V, I, L, M; D, E; N, Q; S, T; K, R, H; F, Y, W, H; and P, Nα-alkylamino acids.

TABLE 1

Exemplary conservative amino acid substitutions

| | Conservative Substitutions |
|---|---|
| Ala | Val*, Leu, Ile |
| Arg | Lys*, Gln, Asn |
| Asn | Gln*, His, Lys, Arg, Asp |
| Asp | Glu*, Asn |
| Cys | Ser |
| Gln | Asn*, His, Lys, |
| Glu | Asp*, γ-carboxyglutamic acid (Gla) |
| Gly | Pro |
| His | Asn, Gln, Lys, Arg* |
| Ile | Leu*, Val, Met, Ala, Phe, norleucine (Nle) |
| Leu | Nle, Ile*, Val, Met, Ala, Phe |
| Lys | Arg*, Gln, Asn, ornithine (Orn) |
| Met | Leu*, Ile, Phe, Nle |
| Phe | Leu*, Val, Ile, Ala |
| Pro | Gly*, hydroxyproline (Hyp), Ser, Thr |
| Ser | Thr |

TABLE 1-continued

Exemplary conservative amino acid substitutions

| | Conservative Substitutions |
|---|---|
| Thr | Ser |
| Trp | Tyr |
| Tyr | Trp, Phe*, Thr, Ser |
| Val | Ile, Leu*, Met, Phe, Ala, Nle |

*indicates preferred conservative substitutions

In a fourth aspect, the present invention provides a method for the therapeutic or prophylactic treatment of protocadherin 19 (PCDH19) protein deficiency or altered PCDH19 protein function in a subject, wherein said method comprises the step of:
(i) administering to said subject: a polynucleotide molecule comprising a nucleotide sequence showing at least 70% sequence identity to the complete protocadherin 19 (PCDH19) open reading frame (ORF) nucleotide sequence according to SEQ ID NO: 1, wherein said nucleotide sequence encodes a functional PCDH19 protein or polypeptide, or a functional fragment or functional variant thereof; a functional PCDH19 protein or polypeptide, or functional fragment or functional variant thereof encoded by a polynucleotide molecule comprising a nucleotide sequence showing at least 70% sequence identity to the complete PCDH19 ORF nucleotide sequence according to SEQ ID NO: 1; and/or an agent that compensates for the loss of PCDH19 protein function; optionally in combination with a pharmaceutically-acceptable carrier.

Preferably, the method comprises administering a functional PCDH19 protein or polypeptide comprising an amino acid sequence according to SEQ ID NO: 2, or a functional fragment or functional variant thereof.

Alternatively or additionally, the method comprises administering an agent that compensates for the loss of PCDH19 function in the subject. Preferably, such an agent is a protein or polypeptide that compensates for PCDH19 function, such as another protocadherin/cadherin protein, or a functional fragment or functional variant thereof. An example of a preferred compensatory agent is PCDH11Y.

It is envisaged that the method of the fourth aspect may include the administration of whole cells or recombinant delivery vehicles (eg viral vectors). Suitable polynucleotide molecule-delivery vectors include those suitable for the chromosomal integration of the polynucleotide molecule of the present invention (eg retroviral vectors), or simply for the non-integrated expression of the polynucleotide molecule (eg plasmid vectors). Alternatively, the administration of a polynucleotide molecule encoding a PCDH19 protein or polypeptide, or functional fragment or functional variant thereof, may involve any of the methods and/or agents for the delivery of "naked DNA" to cells well known to persons skilled in the art (eg liposomes, lipoplexes, polyplexes, gold microparticles, and conjugation to mannose and the like).

In a fifth aspect, the present invention provides an agent capable of treating a deficiency in functional protocadherin (PCDH19) protein or altered PCDH19 protein function in a subject.

Preferred agents according to the fifth aspect include: a polynucleotide molecule comprising a nucleotide sequence showing at least 70% sequence identity, preferably at least 85% sequence identity, and, more preferably, at least 95% sequence identity to the complete PCDH19 ORF nucleotide sequence according to SEQ ID NO: 1; or a functional PCDH19 protein or polypeptide, or functional fragment or functional variant thereof encoded by a polynucleotide molecule comprising a nucleotide sequence showing at least 70% sequence identity, preferably at least 85% sequence identity, and, more preferably, at least 95% sequence identity to the complete PCDH19 ORF nucleotide sequence according to SEQ ID NO: 1. Most preferably, the agent is a polynucleotide molecule comprising a nucleotide sequence encoding a PCDH19 protein or polypeptide comprising the amino acid sequence shown as SEQ ID NO: 2; or a functional PCDH19 protein or polypeptide comprising the amino acid sequence shown as SEQ ID NO: 2.

Further preferred agents include an isolated or recombinantly expressed PCDH11Y protein or polypeptide, or a functional fragment or functional variant thereof. Homologues, analogues, orthologues or mimetics of PCDH19 or PCDH11Y may also be suitable and, indeed, these may possess further desirable characteristics for use as therapeutic agents, for example in vivo stability, safety and toxicity, pharmaceutical acceptability and the like. The selection of preferred homologues, analogues, orthologues or mimetics of PCDH19 or PCDH11Y according to desirable characteristics may be readily determined by methods well known to persons skilled in the art.

Particularly preferred agents according to the fifth aspect are agents that are capable of providing treatment to EFMR or prophylactic treatment to subjects predisposed to EFMR.

Agents of the fifth aspect may be administered with a pharmaceutically acceptable carrier, and/or formulated into any suitable pharmaceutical/veterinary composition or dosage form (eg compositions for oral, buccal, nasal, intramuscular and intravenous administration). Typically, such a composition or dosage form will be administered to the subject in an amount which is effective to treat EFMR or provide prophylaxis to a subject predisposed to EFMR, and may therefore be provided at between about 0.01 and about 100 µg/kg body weight per day of the agent, and more preferably, at between 0.05 and 25 µg/kg body weight per day of the agent. A suitable composition may be intended for single daily administration, multiple daily administration, or controlled or sustained release, as needed to achieve the most effective result.

In a sixth aspect, the present invention provides a method for identifying an agent capable of treating a deficiency in functional protocadherin 19 (PCDH19) protein or altered PCDH19 protein function, wherein said method comprises the steps of;
  (i) providing a cell or animal comprising a polynucleotide molecule comprising a mutant sequence of the PCDH19 ORF nucleotide sequence shown as SEQ ID NO: 1;
  (ii) contacting a test agent with said cell or administering a test agent to said animal; and
  (iii) comparing a response in said cell or animal with a control response.

The method of the sixth aspect may identify agents capable of providing a treatment of illness caused by a deficiency in functional PCDH19 protein or altered PCDH19 protein function, or which may be capable of providing a prophylactic treatment of functional PCDH19 protein deficiency or altered PCDH19 protein function.

The control response referred to in step (iii) of the method may include a baseline response detected in said cell or animal without exposure to the test agent or, alternatively, the control response may be a response following exposure to the test agent in cells or animals comprising a normal or wild-type complete PCDH19 ORF nucleotide sequence.

The test agent may be selected from known and novel compounds, complexes and other substances which may, for example, be sourced from private or publicly accessible agent libraries (eg the Queensland Compound Library (Griffith University, Nathan, QLD, Australia) and the Molecular Libraries Small Molecule Repository (NIH Molecular Libraries, Bethesda, MD, United States of America). The test agent may therefore comprise a protein, polypeptide or peptide (eg a recombinantly expressed PCDH19 or PCDH11Y protein or polypeptide, or a functional fragment or functional variant thereof), or a mimetic thereof (including so-called peptoids and retro-inverso peptides), but more preferably comprises a small organic molecule and especially one which complies or substantially complies with Lipinski's Rule of Five for "druglikeness" (Lipinski, C A et al., 2001). The test agent may also be selected on the basis of structural analysis of known or novel compounds or may otherwise be designed following the further structural analysis of PCDH19 or PCDH11Y binding sites, particularly calcium ion binding sites.

The method of the sixth aspect may be adapted for high-throughput screening of large numbers of test agents.

The step of comparing a response in said cell or animal with a control response may be conducted using one or more standard binding assay formats (eg ELISA-based or competition-based assays). Preferably, the test agent will be labelled with a readily detectable label (eg a fluorochrome or radioisotope) to allow detection of binding to, for example, a calcium channel receptor. A change in activity may be observed in such assays by using standard methods including spectrophotometric, fluorimetric, calorimetric or chemiluminescent means preferably providing for the automation or partial automation of the detecting step (eg by a microplate reader or use of a flow cytometer).

Preferred steps for comparing a response in an animal with a control animal (ie comprising a normal or wild-type complete PCDH19 ORF nucleotide sequence) involve the identification of a disease state in said animal, in particular, the analysis of neurological indicators of illness.

In a seventh aspect, the present invention provides a kit for use in the method of the sixth aspect, wherein said kit comprises instructions for the operation of the method together with one or more containers and/or vessels containing one or more cell(s) or animal(s) comprising a polynucleotide molecule comprising a mutant sequence of the protocadherin 19 (PCDH19) ORF nucleotide sequence shown as SEQ ID NO: 1.

In an eighth aspect, the present invention provides a kit for identifying an agent capable of treating a deficiency in functional protocadherin 19 (PCDH19) protein or altered PCDH19 protein function, wherein said kit comprises;
  (i) a cell or animal comprising a polynucleotide molecule comprising a mutant sequence of the PCDH19 ORF nucleotide sequence shown as SEQ ID NO: 1; and optionally,
  (ii) a control cell or animal comprising a polynucleotide molecule comprising a wild-type form of the complete PCDH19 ORF nucleotide sequence shown as SEQ ID NO: 1, said wild-type form encoding a functional PCDH19 protein or polypeptide, or a functional fragment or functional variant thereof.

The kit of the seventh or eighth aspect may further comprise means for comparing a response in said mutant cell or animal with a control response (eg as caused by a test agent), means for detecting a response (eg adhesiveness of PCDH19 or impaired calcium ion binding in the mutant cell or animal) and, for example, a test agent, and other components as are well known to persons skilled in the art including, for example, wash buffers, stabilisation buffers or other reagents.

In a ninth aspect, the present invention provides an isolated protein or polypeptide comprising an amino acid sequence encoded by a nucleotide sequence showing at least 70% sequence identity to a complete protocadherin 19 (PCDH19) ORF nucleotide sequence according to SEQ ID NO: 1, or a functional fragment or variant thereof.

As used herein, the term "isolated", when used in relation to a protein or polypeptide, or a functional fragment or variant thereof, or when used in relation to a polynucleotide molecule, is to be understood as referring to the protein, polypeptide, functional fragment, variant or polynucleotide molecule in a form that is essentially free of whole cells, components thereof and/or other exogenous cellular or biological materials such as exogenous proteins, polypeptides, peptides and nucleic acid molecules. As such, an isolated protein, polypeptide, functional fragment, variant or polynucleotide molecule, in accordance with the present invention, may be present in a preparation comprising no more than 10% (by weight) of exogenous cellular or biological materials, and may be prepared by any of the methods well known to persons skilled in the art.

Preferably, the protein or polypeptide comprises an amino acid sequence showing at least 75% sequence identity to the complete PCDH19 amino acid sequence shown as SEQ ID NO: 2 and at least 65% sequence identity to the amino acid sequence corresponding to the extracellular cadherin (EC) domain.

More preferably, the protein or polypeptide, or functional fragment or variant thereof, comprises an amino acid sequence showing at least 85% sequence identity and, still more preferably, at least 95% sequence identity to the complete PCDH19 amino acid sequence shown as SEQ ID NO: 2. Most preferably, the protein or polypeptide comprises an amino acid sequence according to SEQ ID NO: 2.

In a preferred embodiment of the ninth aspect, the present invention provides a variant, preferably a non-functional variant, of the amino acid sequence shown as SEQ ID NO: 2 including one or more amino acid mutations. Particularly preferred mutations included within such a variant include one or more amino acid mutations selected from the following changes to the amino acid sequence shown as SEQ ID NO: 2; V441E, Q85X, S671X, L667fsX717, N557K, I119fsX122 and P364fsX375.

The isolated protein or polypeptide, functional fragment or variant thereof, may be isolated from tissues derived from whole organisms (eg biopsied tissues), from cultured tissues (eg cultured fibroblasts), or from other recombinant expression systems. This may involve any of the methods for isolating proteins or polypeptides well known to persons skilled in the art, including ion exchange, chromatography electrophoresis, isoelectric focusing, adsorption chromatography, paper chromatography, reverse-phase chromatography, hydrophobic interaction chromatography, dialysis, ultrafiltration, gel electrophoresis, gel filtration, and ultracentrifugation.

Suitable techniques for expressing a recombinant protein or polypeptide, functional fragment or variant thereof according to the present invention are well known to persons skilled in the art and include, for example, techniques for expressing recombinant His-tagged PCDH19 from a suitable expression vector or cassette using a suitable host cell (eg CHO cells and BL21 cells). Thereafter, the His-tagged expression products can readily isolated using affinity chromatography (eg using a Ni-NTA column (Qiagen Inc, Valencia, CA, United States of America)). Where a functional fragment is to be provided, isolated recombinant protein or polypeptide may be cleaved using a proteolytic enzyme (eg trypsin).

Proteins, polypeptides, variants or, in particular, functional fragments according to the present invention may optionally be incorporated into synthetic proteins or polypeptides such as fusion proteins. Fusion proteins may include components that assist in the production or downstream processing (eg a protein, polypeptide, functional fragment or variant thereof, may be linked to a secretory signal peptide, affinity purification tag or the like).

In a tenth aspect, the present invention provides an isolated polynucleotide molecule comprising a nucleotide sequence showing at least 70% sequence identity to the complete protocadherin 19 (PCDH19) ORF nucleotide sequence according to SEQ ID NO: 1 or a complementary sequence thereto.

Preferably, the polynucleotide molecule comprises a nucleotide sequence showing at least 85% sequence identity and, more preferably, at least 95% sequence identity to the complete PCDH19 ORF nucleotide sequence shown as SEQ ID NO: 1. Most preferably, the polynucleotide molecule comprises a nucleotide sequence as shown as SEQ ID NO: 1.

A polynucleotide molecule of the present invention may encode a protein or polypeptide comprising the amino acid sequence according to SEQ ID NO: 2, or a functional fragment or variant thereof. Alternatively, a polynucleotide molecule of the present invention may otherwise encode a non-functional PCDH19 mRNA (eg an mRNA including a premature termination codon which is degraded by NMD processes) or altered PCDH19 mRNA. Other examples of polynucleotide molecules according to the present invention are oligonucleotide probe/primer molecules which consist of 10 to 50 contiguous nucleotides and, more preferably, about 15 to 30 contiguous nucleotides of the complete PCDH19 ORF nucleotide sequence shown as SEQ ID NO: 1.

Where the polynucleotide molecule comprises a nucleotide sequence showing at least 70% sequence identity, preferably at least 85% sequence identity and, more preferably, at least 95% sequence identity to the nucleotide sequence shown as SEQ ID NO: 1, it will be appreciated that such a polynucleotide molecule may vary from that nucleotide sequence only in minor changes which, for example, do not result in a significant alteration in an encoded protein or polypeptide due to degeneracy in the DNA code or which may be required in order to enhance expression in a particular system (ie to comply with preferred codon usage). Further, it will be appreciated that such a polynucleotide molecule may otherwise encode a variant of a protein or polypeptide comprising the amino acid sequence shown as SEQ ID NO: 2 which shows enhanced or reduced biological activity (eg a variant including one or more amino acid mutations in the extracellular cadherin (EC) domain and showing reduced adhesiveness through impaired calcium ion binding). Indeed, in an embodiment of the tenth aspect, the present invention provides a polynucleotide molecule encoding a variant, preferably a non-functional variant, including one or more amino acid substitutions, additions or deletions in the extracellular cadherin (EC) domain and showing reduced adhesiveness through impaired calcium binding. Particularly preferred mutations encoded by such polynucleotide molecules include one or more of the following changes to the amino acid sequence shown as SEQ ID NO: 2; V441E, Q85X, S671X, L667fsX717, N557K, I119fsX122 and P364fsX375. With reference to the complete PCDH19 ORF nucleotide sequence shown as SEQ ID NO: 1, the mutations responsible for such amino acid sequence changes may be, respectively; 1322 T>A, 253 C>T, 2012 C>G, 2030_2031insT, 1671 C>G, 357delC and 1091_1092insC.

The polynucleotide molecule of the present invention may be used to express an encoded protein or polypeptide, or functional fragment or variant thereof, by recombinant methodologies involving cloning of the polynucleotide molecule into a suitable expression cassette or vector and thereafter introducing the expression cassette or vector into a suitable host cell. Suitable expression vectors may include functional sequences such as a multiple cloning site, a detection tag (eg glutathione-S-transferase (GST) or green fluorescent protein (GFP)), a tag for downstream purification (eg a histidine tag (His)), linker and fusion sequences.

In an eleventh aspect, the present invention provides a cell transformed with the polynucleotide molecule of the tenth aspect.

The polynucleotide molecule may comprise a mutant sequence of the PCDH19 ORF nucleotide sequence shown as SEQ ID NO: 1, and thereby encode non-functional or altered PCDH19 mRNA, non-functional PCDH19 protein or a PCDH19 protein with altered function, or which otherwise causes reduced expression of PCDH19 protein, or a complementary sequence thereto.

The polynucleotide molecule may also consist or encode an antisense RNA, ribozyme, DNAzyme or interfering RNA molecule (eg siRNA) targeted to PCDH19.

The transformed cell may be selected from bacterial cells, insect cells and mammalian cells. The cell may be transformed using any of the methods well known to persons skilled in the art including direct uptake, transduction, f-mating or electroporation. The transformed polynucleotide molecule may be maintained in a non-integrated form (eg in a non-integrated plasmid expression vector), or alternatively, may be integrated into the genome of the transformed cell.

The transformed cell can be employed in a variety of applications that will be readily apparent to persons skilled in the art, in particular, for the generation of an isolated recombinant protein or polypeptide, or functional fragment or variant thereof according to the present invention.

Where the transformed cell is intended for the production and harvest of a PCDH19 protein or polypeptide, functional fragment or variant thereof, the expression of the recombinant product can be determined by, for example, Western immunoblot assays for the direct detection of the protein or polypeptide, functional fragment or variant thereof, or for detection of an expression tag (eg a His tag). In a twelfth aspect, the present invention provides a non-human animal comprising the polynucleotide molecule of the tenth aspect.

The polynucleotide molecule may comprise a mutant sequence of the PCDH19 ORF nucleotide sequence shown as SEQ ID NO: 1, and thereby encode non-functional or altered PCDH19 mRNA, non-functional PCDH19 protein or a PCDH19 protein with altered function, or which otherwise causes reduced expression of PCDH19 protein, or a complementary sequence thereto.

The polynucleotide molecule may also consist or encode an antisense RNA, ribozyme, DNAzyme or interfering RNA molecule (eg siRNA) targeted to PCDH19.

The polynucleotide molecule is preferably uniformly integrated throughout the animal's tissues. Where a chimeric animal is provided, the polynucleotide molecule is preferably present in cells of the animal's nervous tissues.

The polynucleotide molecule may be introduced into the animal by any of the methods of transformation or transgenesis well known to persons skilled in the art. Such transformation methods include DNA transfection (via electroporation, liposome or protoplast fusion, or microinjection), infection with viral delivery vectors (ie vectors that facilitate genomic integration such as adenoviral and retroviral vectors), or via random mutagenesis followed by the selection of desired mutations by screening. However, the animal of the present invention will generally be preferably generated by micro-injection methodologies. To ensure the genetic uniformity of resulting transgenic animals, microinjection is preferably performed at the one-cell embryo stage by any of the methods well known to persons skilled in the art. Preferred transgenic animals include rodents, in particular mice and rats.

The animals of the eleventh aspect can be employed in a variety of applications that will be readily apparent to persons skilled in the art, in particular, for use as in vitro or in vivo disease models for use in methods or kits for screening potential agents to compensate for PCDH19 protein deficiency or altered PCDH19 protein function.

In a further aspect, the present invention provides an antibody or fragment thereof which specifically binds to the protein or polypeptide, functional fragment or variant thereof, of the ninth aspect.

Suitable antibodies include monoclonal and polyclonal antibodies. Suitable antibody fragments include fragments produced by enzymatic cleavage of antibodies such as Fab and $F(ab')_2$ fragments, and recombinant antibody fragments such as single chain Fv (scFv) fragments.

The antibody or fragment thereof may be capable of distinguishing between, for example, a wild-type PCDH19 protein (ie comprising the complete PCDH19 amino acid sequence shown as SEQ ID NO: 2) and a variant thereof, particularly, a non-functional variant thereof. Thus, the present invention extends to an antibody or fragment thereof that specifically binds to a variant of the complete PCDH19 amino acid sequence shown as SEQ ID NO: 2.

The present invention is hereinafter further described by way of the following, non-limiting example and accompanying figures.

Example

Materials and Methods

Patient and Family Details

Individuals from seven families with family members suffering from epilepsy and mental retardation limited to females (EFMR) were admitted. The clinical details of Families 1-4 are described in Scheffer I E et al. (2007). Family 5 was screened on the basis of one sister having infantile seizures and Asperger syndrome and her sister having epilepsy and mild intellectual disability. The clinical details of members of Family 6 and Family 7 are described elsewhere (Juberg R C and Hellman C D, 1971; Fabisiak K and Erickson R P, 1990; and Ryan S G et al., 1997).

Northern Blotting

Human brain (MTN) blot II and V (acquired from Clontech Laboratories) were hybridised according to the manufacturer's instructions. Detection assays utilised a probe containing nucleotides 2884-3257 of human PCDH19 ORF (NCBI accession number 921478). The primers used to generate the probe were:

```
forward primer - 5'CCGGATTCTTGGCCACTCTGAC3';    (SEQ ID NO: 3)
and reverse primer - 5'CAATGGTGTAAGACACGGAAG3'.    (SEQ ID NO: 4)
```

The 374 bp probe was labelled with radioactive α32P-dCTP (Perkin Elmer, Waltham, MA, United States of America) using the Mega prime DNA labelling system (GE Healthcare, Piscataway, NJ, United States of America).

RT-PCR Analyses

Total RNA was extracted from fibroblast cells using the RNeasy mini kit (Qiagen, Doncaster, VIC, Australia), and treated with DNase I (Qiagen). 2 µg of RNA was primed with 1 µg of random hexanucleotides and subjected to reverse-transcription for 90 minutes at 42° C. using Superscript II according to the maufacturer's instructions (Invitrogen Corporation, Carlsbad, CA, United States of America). The efficiency of the reaction was tested by PCR using primers specific to the ubiquitously expressed ESD gene (Saviozzi et. al., 2006). cDNAs were amplified with Taq DNA polymerase (Roche, Basel, Switzerland) and specific single-stranded DNA primers for 35 cycles (denaturation, 94° C. for 30 seconds; annealing, at specific Tm for each pair of primers for 30 seconds; extension, 72° C. for 30 seconds). PCR products were separated by agarose gel electrophoresis and stained with 1% ethidium bromide for visualisation under UV.

Tissue Culture—Primary Skin Fibroblast Lines

A 3 mm skin biopsy excised from the upper arm of each subject was cut finely and transferred to a tissue culture flask. The biopsy was cultured in RPMI medium with 20% foetal calf serum (FCS) (further supplemented with 4 mM L-Glutamine, 0.017 mg/ml benzylpenicillin) and grown at 37° C. with 5% $CO_2$. Once established, fibroblasts where cultured in RPMI with 10% FCS (also including the supplements described above).

Cycloheximide Treatment of Skin Fibroblast Cell Lines

Primary fibroblast cells were seeded $1 \times 10^4/cm^2$ in RPMI with 10% FCS and incubated with 50 µg/ml cycloheximide (Sigma-Aldrich Co, St Louis, MO, United States of America), or media alone, for 6 hrs. Fibroblasts were harvested using a sterile cell scraper (Techno Plastic Products AG, Trasadingen, Switzerland), then washed once in phosphate buffered saline (PBS) prior to total RNA extraction and reverse transcription to generate cDNA as described above.

Mouse In Situ Hybridisation Analysis 15.5 days postcoital (dpc) embryonic heads and dissected postnatal day 2 (P2) brains from c57×CBAF1 mice were fixed in 4% paraformaldehyde at 4° C., cryoprotected in 30% sucrose and frozen in optimal cutting temperature (OCT). In situ hybridisation of 16 µM sections was performed as described previously (Wilson L D et al., 2005) using a digoxygenin-labelled PCDH19 antisense RNA probe, prepared as previously described (Gaitan Y and Bouchard M, 2006). A total of three neonates and two embryos were analysed and representative sections were documented. No signal was detected in negative controls, which utilised a sense control probe. Images were taken on a Zeiss Axiophot microscope, compiled and minimally processed (adjusted for colour and light/dark) using Adobe Photoshop CS®.

Semi-Quantitative RT-PCR

Gene expression profiles were generated using Rapid-Scan Gene Expression Human Brain cDNA panels (Origene Technologies, Inc, Rockville, MD, United States of America) containing first strand cDNA prepared from polyA+ RNA. The cDNA panels allow semi-quantitative analysis due to the cDNAs being serially diluted over a 4-log range. The profiles were obtained from panels containing approximately 1 ng of first strand cDNA. The PCR primer pair;

X-RT4F2—5' GTA ACA AGT GTA CCT GGT ATG GAC T 3' (SEQ ID NO: 5) and

X-RT5R2—5' TCA ACC TTT ACT TTC ATC ACG 3' (SEQ ID NO: 6), were used to amplify the PCDH11X sequence to yield a 683 bp product, and the primer pair;

Y-RT4F—5' TAC AAC AAA CTG TCA CAA GTG TTT 3' (SEQ ID NO: 7), and

Y-RT5R2—5' TCA ACC TTT ACT TTC ATC ACA 3' (SEQ ID NO: 8), were used to amplify PCDH11Y to yield a 681 bp product. The primers;

WLF—5' AAC CAG AAT ACC CGC AAC AC 3' (SEQ ID NO: 9) and

WLR—5' CTG CAG ATG GTC ACA TCG AC 3' (SEQ ID NO: 10), were used to amplify PCDH19 to yield a 626 bp product.

The PCR conditions used to amplify the PCDH19 product comprised an initial step at 94° C. for 3 minutes, followed by 35 cycles at 94° C. for 30 seconds, 60° for 30 sec and 72° C. for 2 mins. The PCDH11X and PCDH11Y products were amplified using Hotstar Taq (Qiagen) according to the Hotstar recommended cycling conditions (94° C. for 15 minutes followed by 10 cycles at [94° for 30 sec, 60° for 30 sec, 72° for 1 min] and then 30 cycles at [94° for 30 sec, 55° for 30 sec, 72° for 1 min] followed by 72° C. for 10 min).

GenBank Accession Numbers

Where available, partial nucleotide and amino acid sequences were accessed from the GenBank library. The accession numbers corresponding to these sequences are:

incomplete human PCDH19 mRNA accession number NM_020766.1;

incomplete human PCDH19 protein accession number NP_065817.1; and complete human PCDH19 mRNA and protein accession number GenBank EF676096.

The GenBank library can be accessed at the following URLs;

NCBI: http://www.ncbi.nlm.nih.gov/, or Ensembl: http://www.ensembl.org/.

Nucleotide and amino acid sequences were determined by standard di-deoxy chain termination sequencing methods as described in Sambrook, J., Fritsch, E. F., and Maniatis, T., *Molecular Cloning: A Laboratory Manual*. Cold Spring Harbor Laboratory Press, NY, Vol 1, 2, 3 (1989).

Results and Discussion

Genetic Linkage Analysis and Identification of EFMR Gene

As a follow up to previous studies in which a single large American family with EFMR was described (Juberg R C and Hellman C D, 1971; Fabisiak K and Erickson R P, 1990; and Ryan S G et al., 1997), four new EFMR families were identified based on the inheritance pattern of EFMR, the electroclinical features of family members and the localisation of the gene responsible for EFMR (Scheffer I E et al., 2004; Scheffer I E et al., 2007).

Pedigrees of the seven EFMR families in total were generated, which showed the characteristic inheritance pattern of affected females and transmitting males (FIG. 1).

Further linkage analysis within families showed that the disease condition in each family consistently localised to Xq22.

The EFMR gene was identified from re-sequenced 737 VEGA annotated X-chromosome genes in probands from three families. In all three families, each of the X chromosomes encoded protocadherin 19 (PCDH19) mutations (X$^m$) which were found to co-segregate with the EFMR clinical phenotype. The PCDH19 gene was known to be located at Xq22 (Ensembl) within the original linkage region (Ryan S G et al., 1997). An example of a sequence chromatogram of a PCDH19 mutation as detected in an affected female from each family is shown alongside the pedigrees in FIG. 1.

Sequence analysis of family members showed a single nonsense nucleotide change 2012C>G (residue S671X) in the PCDH19 gene in Family 3, while Families 1 and 2 initially did not show any changes (FIG. 1). There were no other deleterious nucleotide changes identified in the three families for which the other 736 genes were screened. Subsequent comparative sequence analysis of the annotated PCDH19 open reading frame (ORF) (accession number NM_020766.1) revealed that it was incomplete. This prompted the sequencing of the additional N-terminal 1.5 kb of PCDH19 ORF.

N-terminal sequencing of family members identified a missense change, 1322T>A (residue V441E) in Family 1, a nonsense change, 253C>T (residue Q85X) in Family 2 and a putative frameshift change, 2030_2031 insT (residues L667fsX717) in Family 4. The N-terminal PCDH19 region in affected females from an unreported Irish EFMR family (Family 5) was also sequenced resulting in the identification of a frameshift change, 375delC (residues I119fsX122). The PCDH19 N-terminal region from the original, large American EFMR family (Family 6) was re-sequenced resulting in the identification of a further frameshift mutation 1091_1092insC (residue P364fsX375) (Juberg R C and Hellman C D, 1971; Fabisiak K and Erickson R P, 1990; Ryan S G et al., 1997) (FIG. 1). Finally, a nucleotide change 1671 C>G was identified in Family 7, coding for an amino acid substitution of N557K.

Once aligned, silent nucleotide changes were further identified between family members and localised to positions 6 (G>A), 348 (G>A), 402 (C>A), 1137 (C>T), 1627 (C>T) and 1683 (G>A) (frequencies shown in Table 2).

TABLE 2

Summary of the nucleotide changes found in PCDH19 (GenBank accession number EF676096) with allele frequencies are indicated in parentheses.

| exon | base change | amino acid position |
|---|---|---|
| 1 | c.6G(99.8%) > A(0.2%) | E2E |
| 1 | c.348G(99.8%) > A(0.2%) | K116K |
| 1 | c.402C(97.1%) > A(2.9%) | I134I |
| 1 | c.1137C(99.0%) > T(1.0%) | G379G |
| 1 | c.1627C(68%) > T (32%) | L543L |
| 1 | c.1683G(99.8%) > A(0.2%) | P561P |

Figure 3:
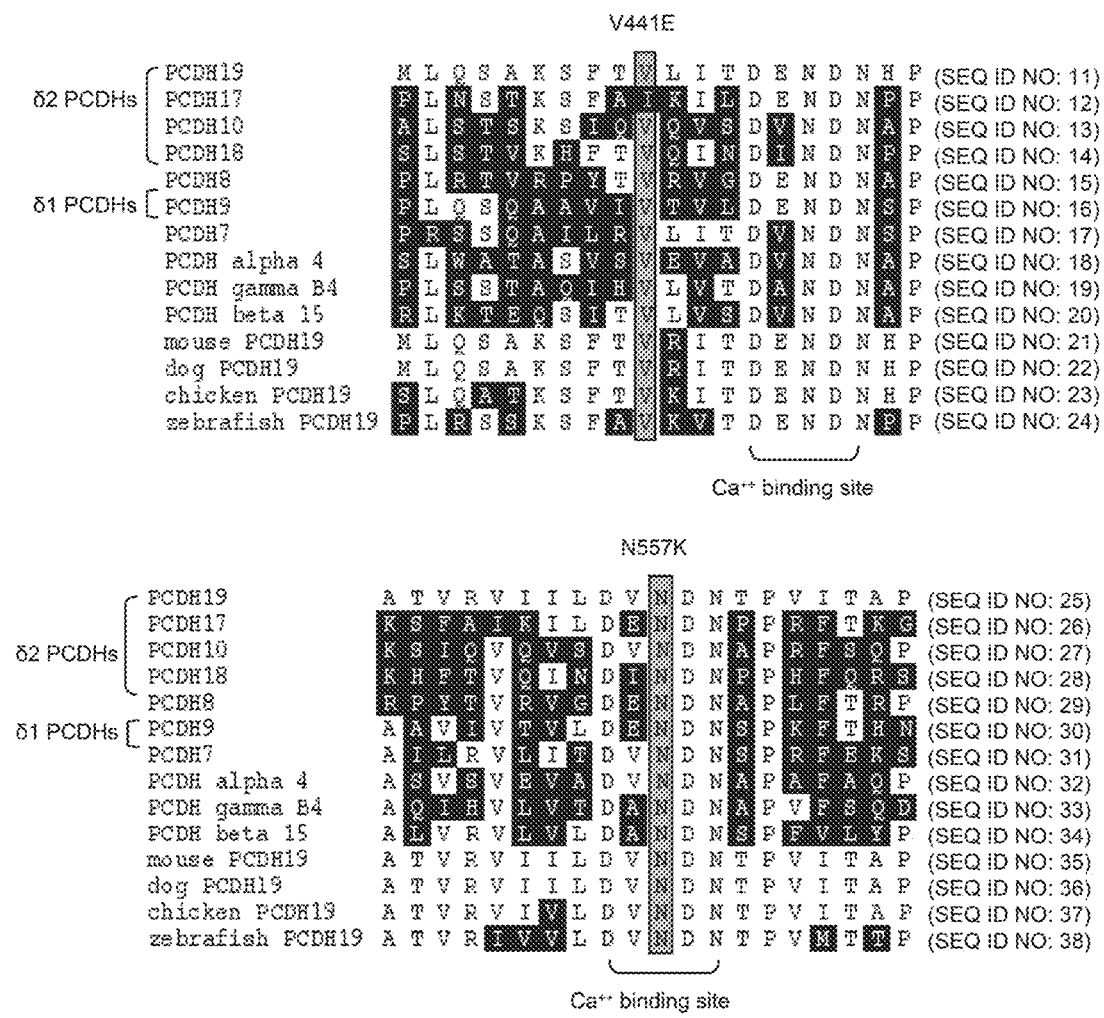
FIG. 3 shows the partial alignment of the human PCDH19 with orthologues of PCDH19 from other species and other human protocadherins. The high conservation of residues affected by two missense mutations, V441E (top panel) and N557K (bottom panel) are indicated by rectangular boxes. The calcium ion-binding acidic residues are also indicated by a bracket against both alignments.

Partial alignment of the human PCDH19 amino acid sequence with other human PCDH sequences and orthologues of PCDH19 from other species demonstrates high conservation of residues affected by the two missense mutations, V441E and N557K, across other species and across other functionally similar proteins (FIG. 3). Mutation V441E was observed in Family 1 and N577K was observed in Family 7.

Accordingly, PCDH19 ORF nucleotide changes were identified in all seven of the assessed EFMR families. All seven nucleotide changes segregated with the clinical phenotype in each EFMR family and were not identified in 250 male probands from families with putative X-linked mental retardation (XLMR) or in 750 control X chromosomes. The positions of the PCDH19 mutations in conjunction with alignments showing the location and conservation of the two missense mutations further demonstrate that PCDH19 mutation is causative of EFMR.

Relationship Between PCDH19 Mutation and Rett Syndrome or Autism

To determine whether PCDH19 mutations also contribute to the presentation of disease conditions with similar phenotypes to EFMR, subjects presenting with Rett syndrome or autism, where no known cause had been determined, were tested for mutations at PCDH19.

Rett syndrome is a female specific disease known to present with a similar phenotype to EFMR. 46 females with apparent Rett syndrome, who were negative for mutations in the two Rett associated genes, MECP2 and CDKL5, were investigated. No nucleotide changes were found in the Rett syndrome cohort, suggesting that PCDH19 mutations are unlikely to commonly contribute to Rett syndrome.

Since autistic features were commonly seen in affected EFMR females, a cohort of 55 females with autism and seizures were screened for changes in PCDH19. The absence of mutations in this cohort suggests that PCDH19 mutations also do not commonly contribute to autism.

Characterisation of the PCDH19 Gene

Figure 4:
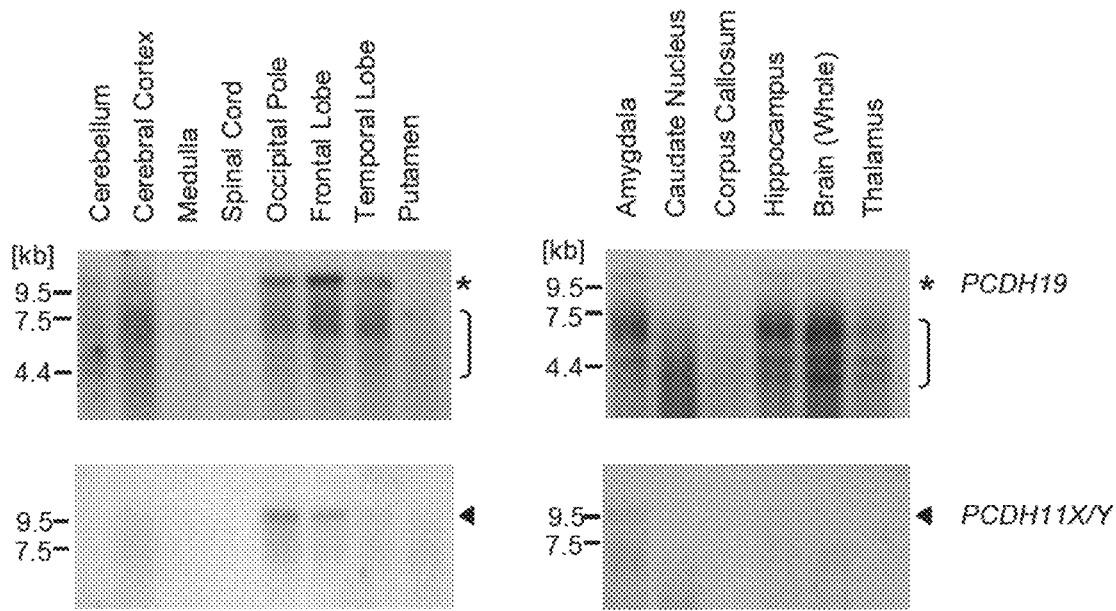
FIG. 4 shows Northern blot (Clontech Laboratories, Inc., Mountain View, CA, United States of America) analyses of PCDH19 and PCDH11X/Y in various human brains tissues. The position of the ~9.8 kb PCDH19 transcript is indicated by an asterisk, while the position of the smaller ~9.5 kb PCDH11X/Y mRNAs is shown by an arrowhead. The brackets indicate either non-specific binding of the PCDH19 probe or PCDH19 degradation products.

The complete 3.447 kb ORF of the PCDH19 gene which consists of 6 exons was annotated (GenBank accession number EF676096). The full-length processed PCDH19 mRNA is 9.765 kb long, this was confirmed by Northern blot analysis which showed a transcript size of approximately 9.8 kb using a PCDH19 specific probe on combined male and female mRNA from various areas of the adult human brain (FIG. 4, PCDH19 mRNA is indicated by an asterisk). PCDH19 exon 2 was found to be alternatively spliced (results not shown).

PCDH19 encodes an 1148 amino acid protein belonging to the protocadherin (PCDH) 52 subclass within the cadherin superfamily. The PCDH19 protein contains a signal peptide, six extracellular cadherin (EC) repeats, a transmembrane (TM) domain and a cytoplasmic region with conserved CM1 and CM2 domains. At FIG. 2, a schematic diagram is shown, illustrating the locations of the PCDH19 amino acid sequence changes of each family with respect to the signal peptide, the extracellular cadherin domain (comprising EC1, EC2, EC3, EC4, EC5 and EC6), the transmembrane domain (TM) and the cytoplasmic (CM1 and CM2) domains of the PCDH19 protein. All seven EFMR mutations identified are located in the large extracellular domain.

The biological role of PCDH19 is not known; however, members of the PCDH family are predominantly expressed in the nervous system and are postulated to be involved in the establishment of neuronal connections and in signal transduction at the synaptic membrane (Wu Q and Maniatis T, 1999; Yagi T and Takeichi M, 2000).

Figure 2:
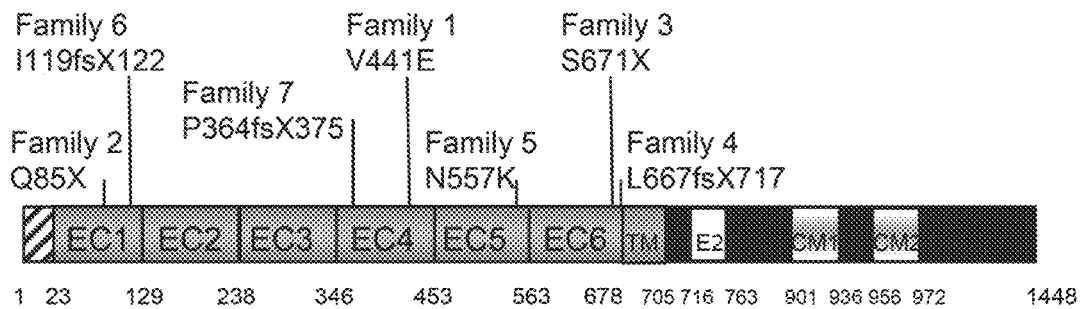
FIG. 2 shows a schematic diagram of the PCDH19 protein with the signal peptide, extracellular cadherin (EC), transmembrane (TM) and cytoplasmic (CM) domains indicated. The relative locations of mutations found in the EFMR families are also shown.

The partial alignments of human and orthologues of PCDH19 from other species, shown at FIG. 3, shows high conservation of residues affected by the two missense mutations, V441E (top panel) and N557K (bottom panel). The N557K mutation affects an invariant asparagine (N) residue within the EC5 domain (FIG. 2). The equivalent asparagine residue of EC1 of classical cadherins (eg N100 of N-cadherin; Patel S D et al., 2006) and protocadherins (eg N101 of CNR/Pcdhα; Morishita H et al., 2006) is essential for calcium ion binding and for adhesive function of the EC1 domain, thus it is expected that tissue mosaicism of PCDH19 negative and PCDH19 wild-type cells scrambles cell-cell communication manifesting clinically as EFMR. The valine residue at position 441 (EC4 in FIG. 2, or the equivalent of V96 of EC1 of N-cadherin; Patel S D et al., 2006; or V97 of EC1 of CNR/Pcdhα; Morishita H et al., 2006) is also highly conserved (FIG. 3) and in close proximity to the calcium binding site (indicated by a bracket against both alignments). Thus, the two missense mutations, V441E and N557K are predicted to lead to loss of PCDH19 function.

Thus, it is predicted that both PCDH19 missense variants adversely affect PCDH19 adhesive function through impaired calcium binding. Given the similarity of the clinical phenotype associated with all seven PCDH19 mutations, it is reasonable to suggest that they all represent loss of function mutations.

Stability of Mutant PCDH19 mRNA Transcripts

The PCDH19 mutations 253C>T, Q85X (Family 2) and 2012C>G, S671X (Family 3) introduce a premature termination codon (PTC) into the PCDH19 mRNA. Such PTC-containing mRNAs are usually recognised by the NMD surveillance complexes and efficiently degraded (Maquat L E, 2004). The consequences of the PCDH19 mutations 253C>T, Q85X (Family 2) and 2012C>G, S671X (Family 3) were examined on the stability of their respective mRNAs by detecting PCDH19 mRNA in primary skin fibroblasts collected from biopsied patients by RT-PCR.

Figure 5:
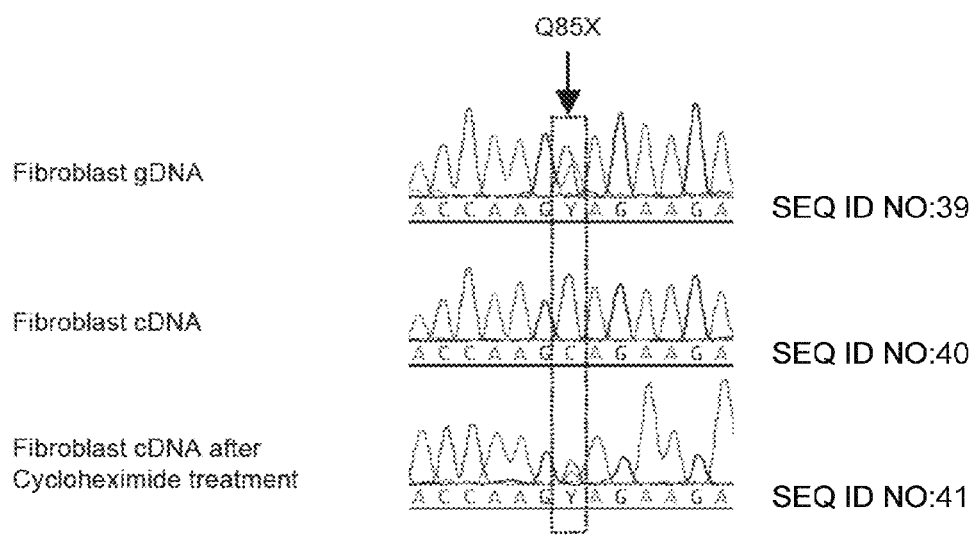
FIG. 5 shows a section of a nucleotide sequence chromatogram from an EFMR affected female, indicating the detection of a mutation, 253C>T, in genomic DNA (gDNA) (top panel), the absence of the mutant sequence in fibroblast cDNA (middle panel) and the presence of both the mutant and wild-type cDNA after the treatment of fibroblasts with cyclohexamide (bottom panel). The position of the mutation is boxed.

FIG. 5 shows a sequence chromatogram from an EFMR affected female from Family 2 showing the detection of the mutation 253C>T, Q85X, in the genomic DNA (gDNA) (top panel), the absence of the mutant sequence in fibroblast cDNA (middle panel) and the presence of both mutant and wild-type cDNA after the treatment of fibroblasts with cycloheximide (bottom panel), which inhibits the pioneer round of translation and leading to NMD. Similar results were found in tissues collected from EFMR affected members of Family 3 (2012C>G mutation, S671X) (data not shown). The inhibition of NMD by cycloheximide treatment of skin fibroblast cells was found to preserve PTC mutation-containing mRNA.

To confirm that the absence of mutant PCDH19 mRNAs was not a consequence of skewing of X-inactivation, random X-inactivation in DNA isolated from blood and skin fibroblast cultures of each affected female available were assessed (data not shown). The absence of X inactivation skewing is in agreement with the published data (Ryan S G et al., 1997; Scheffer I E et al., 2007).

The results demonstrate that the PTC mutations in Families 2 and 3 lead to mRNA removal by NMD. It is anticipated that the mutations at 2030_2031 insT (residues L667fsX717) found in Family 4, 375delC (residues I119fsX122) found in Family 5, and 1091_1092insC (residue P364fsX375) found in Family 6 will also lead to a complete loss of functional mRNA as a consequence of NMD degradation of their respective PTC-containing mRNA.

PCDH19 Expression in the Developing Brain

Figure 6:
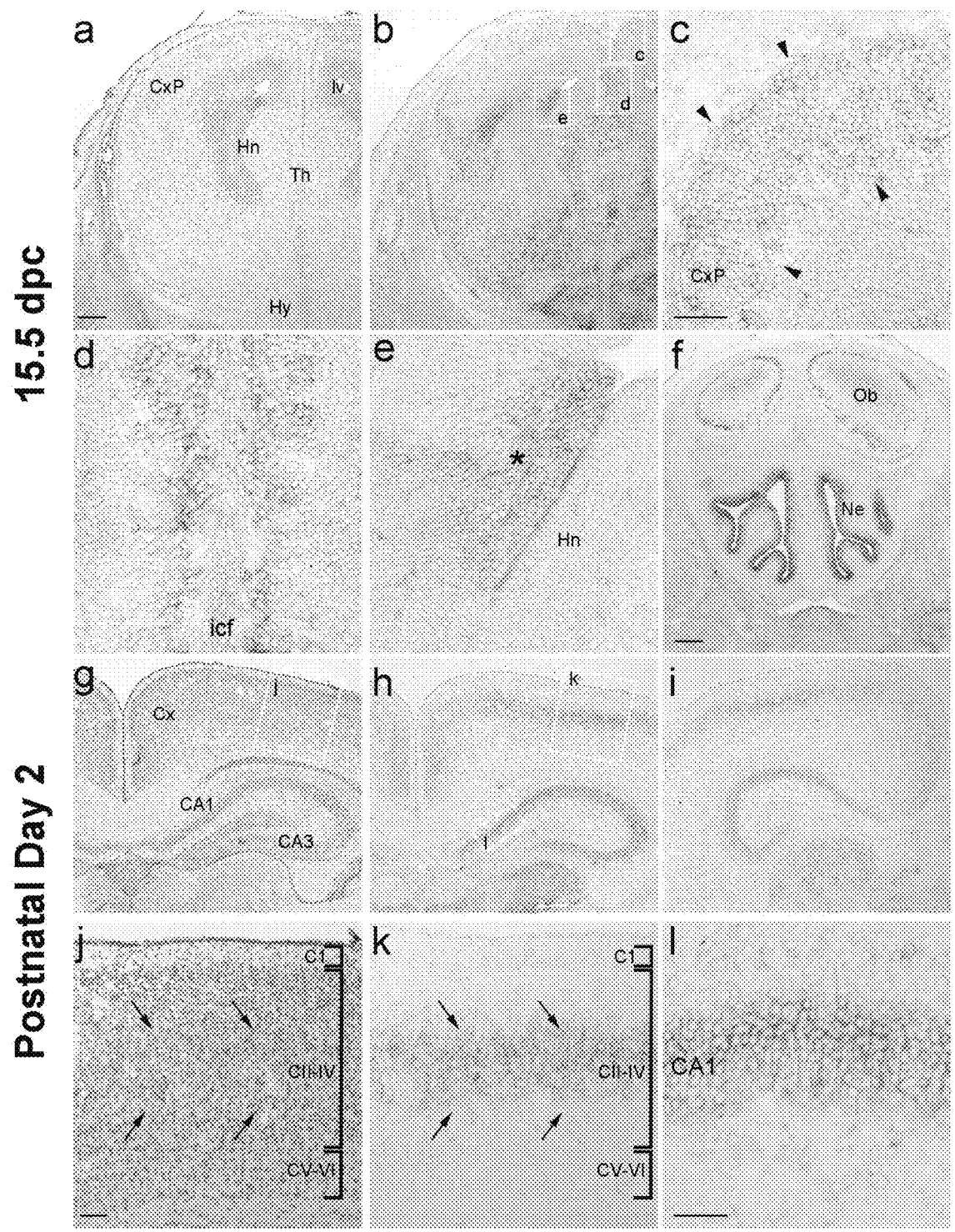
FIG. 6 shows the expression of PCDH19 in murine central nervous system (CNS) at 15.5 days postcoital (a-f) and postnatal day 2 (g-l). (a, b) are adjacent sections stained with Haematoxylin and Eosin and processed for PCDH19 in situ, respectively. (c, d, e) are higher magnification images of the boxed regions in b. Arrowheads in c indicate PCDH19 expressing cells within the cortex; the asterisk in e highlights the dorsolateral wall of the lateral ventricle. (g, h) are adjacent sections stained with Haematoxylin and Eosin and processed for PCDH19 in situ, respectively. (i) is a posterior brain section (to h) highlighting PCDH19 expression. (j, k, l) are higher magnification images of the boxed regions in (g, h, respectively). Cx/P, cortical plate; Hn, Hippocampal neuroepithelium; lv, lateral ventricle; Th, thalamus; Hy, hypothalamus; icf, intercerebral fissure; Ob, olfactory bulbs; Ne, nasal epithelium. Magnification bars (a, b, f-i) represent 200 µM, bars in (c-e; and j-l) represent 50 µM.

To investigate the expression of PCDH19 in the developing murine CNS, in situ hybridisation analysis PCDH19 mRNA in embryonic (15.5 days post coitum (dpc)) and postnatal day 2 tissue was undertaken. FIG. 6 shows the expression of PCDH19 in the developing murine CNS at 15.5 dpc (FIGS. 6a to 6f) and P2 (FIGS. 6g to 6l). FIGS. 6a and 6b show adjacent sections stained with Haematoxylin and Eosin and processed for PCDH19 mRNA in situ, respectively. PCDH19 mRNA was expressed in a widespread, symmetrical pattern in the embryonic forebrain and frequently localised to discrete cell clusters within the cortex (CxP, cortical plate), thalamus (Th) and hypothalamus (Hy). The lateral ventricle (lv) and hippocampal neuroepithelium (Hn) are also indicated. FIGS. 6c, 6d and 6e show higher magnification images of the boxed regions in FIG. 6b. The arrowheads in FIG. 6c indicate PCDH19-expressing cells within the cortex. In the cortex, expression was restricted to the cortical plate and extended medially into the intercerebral fissure (icf) (FIG. 6d). The asterisk in FIG. 6e highlights the dorsolateral wall of the lateral ventricle, robust expression was also detected in the ganglionic eminence that abuts the dorsolateral wall of the lateral ventricles.

At this stage, hippocampal expression was not observed on the medial edge of the lateral ventricle in the presumptive hippocampus (FIGS. 6b and 6e). However, subsequent analysis of anterior forebrain sections revealed PCDH19 expression in the epithelial lining of the nasal cavity (consistent with a previous report (Gaitan Y and Bouchard M, 2006)) and in the olfactory bulbs (see FIG. 6f; olfactory bulbs indicated at Ob and nasal epithelium at Ne).

FIGS. 6g and 6h show adjacent sections stained with Haemotoxylin and Eosin and processed for PCDH19 mRNA by in situ hybridisation, respectively. FIG. 6i shows a brain section posterior with respect to the brain section shown at FIG. 6h, each highlighting PCDH19 mRNA expression. FIGS. 6j, 6k and 6l show higher magnification images of the boxed regions in FIGS. 6g and 6h, respectively.

At postnatal day 2, PCDH19 expression was maintained in discrete regions of the cortex and the thalamus however, unlike the embryonic brain, expression was also observed in the hippocampus (FIGS. 6g, 6h, and 6i). In the cortex, expression was restricted to a band of cells that spanned layers II-IV (indicated by arrows in FIGS. 6j and 6k) whilst the most prominent PCDH19 signal was observed in the CA1 and CA3 regions of the hippocampus (FIGS. 6h and 6l).

Consistent with previous Northern blot analyses (FIG. 2), PCDH19 transcripts were not detected in white matter tracts including the corpus callosum (FIG. 6h). Together these data indicate that PCDH19 has widespread expression in both the embryonic and adult brain including the developing cortex and hippocampus and are consistent with the finding that mutation of this gene in humans is associated with cognitive impairment.

Mechanism for the Observed Disease Inheritance Patterns

Analysis of the EFMR family pedigrees showed that within the seven EFMR families, there are 2 obligate carrier females (Family 6, individual III.2 and Family 7, individual IV.15) who have not been diagnosed with EFMR, indicating the incomplete penetrance of the disorder. Having identified PCDH19 mutations, a mechanistic explanation was sought for the remarkable inheritance pattern observed with EFMR.

One of the hypotheses, considered by Ryan S G et al., 1997, suggests that a dominant negative effect of mutant protein on wild-type protein in females may be responsible for expression of the phenotype being limited to females. In this example, it has been demonstrated that mutant PCDH19 mRNA is removed by NMD in affected females and a carrier male (FIG. 2 and data not shown), which is inconsistent with a dominant negative hypothesis. However, in consideration of an alternative hypothesis (Ryan S G et al., 1997) involving a Y chromosome compensatory gene rescuing transmitting males from the EFMR phenotype, it was noted that while there is no PCDH19 paralogue on the human Y chromosome, there is the related protocadherin gene PCDH11Y within a block of X-Y homology at Xq22. The PCDH11Y gene is thought to have arisen by transposition from Xq after the divergence of chimpanzees and humans (Lambson B et al., 1992; Page D C et al., 1984) and therefore, the PCDH11Y gene is only found in humans and in males.

Figure 8:
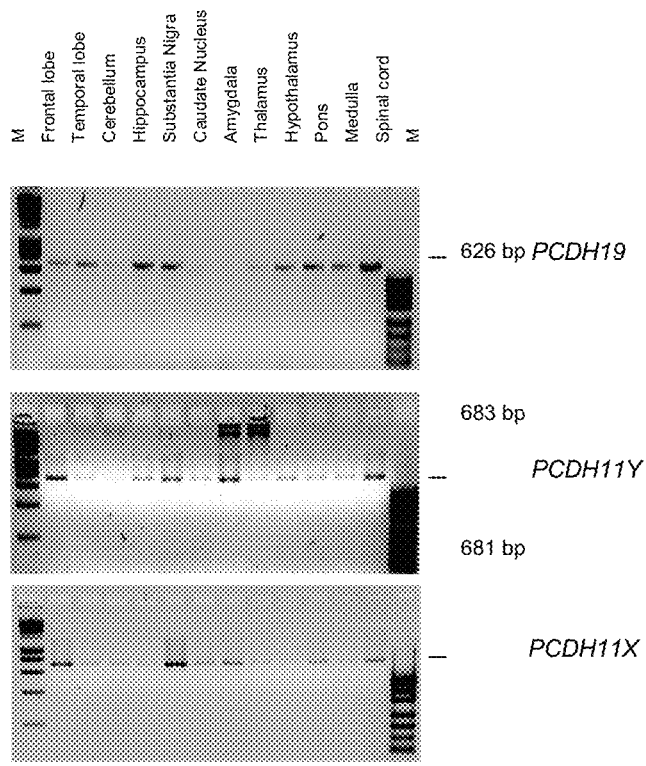
FIG. 8 shows expression profiles of PCDH19 (top panel), PCDH11Y (middle panel) and PCDH11X (bottom panel) in various regions of adult human brain tissues.

A Northern blot analysis of PCDH19 and PCDH11X/Y was conducted in human cerebellum, cerebral cortex, medulla, spinal cord, occipital pole, frontal lobe, temporal lobe, putamen, amygdale, caudate nucleus, corpus callosum, hippocampus, thalamus and whole brain tissues. FIG. 6c shows the presence of PCDH19 transcripts (indicated by an asterisk, approximately 9.8 kb band), and the presence of PCDH11X/Y mRNAs (indicated by an arrowhead, approximately 9.5 kb band). FIG. 8 also shows expression profiles of PCDH19, PCDH11X and PCDH11Y in the adult human Frontal lobe, temporal lobe, cerebellum, hippocampus, substantial nigra, caudate nucleus, amygdale, thalamus, hypothalamus, pons, medulla, and spinal cord. Like many other members of the protocadherin family (Kim S Y et al., 2007) PCDH19, PCDH11Y and PCDH11X are expressed in human brain. PCDH1 IX and PCDH11Y show high sequence similarity, being 98.1% identical at the nucleotide level and 98.3% identical at the amino acid level (Blanco P et al., 2000) and show similar expression profiles in brain regions (Blanco P et al., 2000 and FIG. 8). However, PCDH11X and PCDH11Y have undergone sequence divergence at the 5' and 3' ends of their ORF sequences, are regulated differently and show slight differences in their regions of expression in the brain (Blanco P et al., 2000). It is therefore possible that PCDH11X and PCDH11Y have evolved different functions.

Sequence comparisons show that the extracellular cadherin (EC) domains of both PCDH11X and PCDH11Y have some similarity to the EC domains of PCDH19; a higher level of similarity than that seen between the EC domains of PCDH19 and fellow PCDH d2 subclass members (PCDH-8, 10, 17 and 18).

The high sequence identity and overlap in expression patterns between PCDH11X and PCDH11Y provides support for the hypothesis that PCDH11X compensates for PCDH19 loss of function mutations in females and that both PCDH11X and PCDH11Y compensate for PCDH19 mutations in males.

A uniquely evolved function of PCDH11Y may enable the protein to provide greater rescue of PCDH19 mutations than PCDH11X, which provides rationale for the greater frequency of spared male carriers than females presenting with EFMR.

Figure 7:
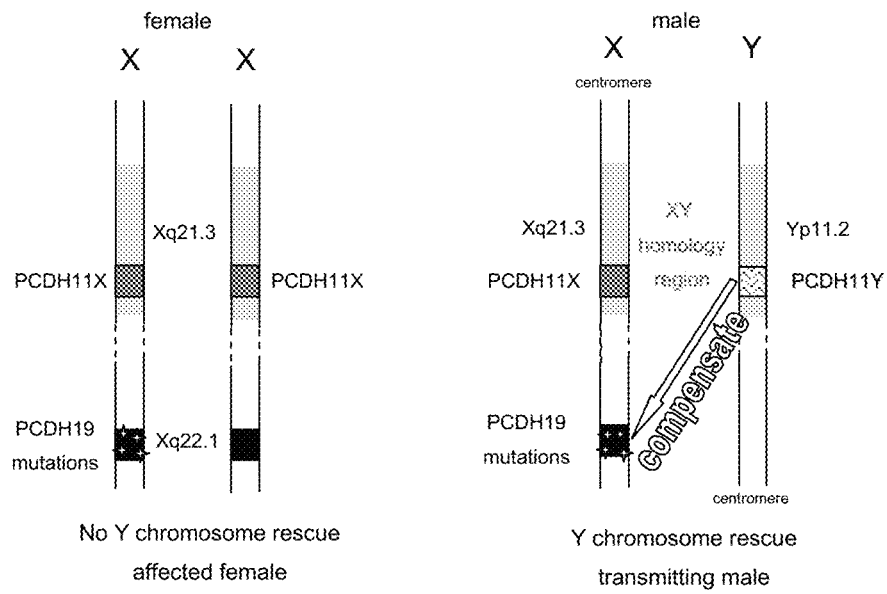
FIG. 7 shows a diagrammatic representation of the expected mechanism underlying the inheritance of EFMR whereby PCDH11Y functionally rescues PCDH19 mutations in transmitting males.

A diagrammatic representation of the proposed mechanism underlying the inheritance of EFMR is illustrated in FIG. 7. The PCDH19 gene is located at Xq22.1 and is now known to harbour EFMR mutations. Within a homology region between the X and Y chromosomes there are two very similar PCDH genes, PCDH11X on the X chromosome and PCDH11Y on the Y chromosome. The results provided herein indicate that PCDH11Y may functionally rescue PCDH19 mutations in transmitting males, while in females PCDH11X is unable to carry out rescue, explaining the EFMR phenotype being limited to females.

The loss of function of all seven of the PCDH19 changes characterised herein, their absence from control chromosomes, the absence of evidence for potential disease-causing variants elsewhere on the X chromosome and the mRNA studies conclusively show that the identified PCDH19 mutations are causative of EFMR. The identification of nucleotide and amino acid sequences corresponding to a complete PCDH19 ORF provide for the development of diagnostic and therapeutic agents for EFMR and similar disorders associated with deficiencies in functional PCDH19 protein. Further, the elucidation of the suspected mechanism of PCDH19 rescue by PCDH11Y provides for the possibility of identifying and developing alternative therapeutic agents for the treatment of illnesses associated with PCDH19 protein-deficiency.

All seven of the characterised EFMR mutations are located in the large extracellular domain and five of these are predicted to be complete loss of function mutations as a consequence of NMD degradation of their respective PTC containing mRNA. The remaining two missense mutations, V441E and N557K are predicted to lead to a loss of PCDH19 function. Loss of function may be the result of impaired calcium ion binding through a lack of PCDH19 adhesiveness. Thus, genetic and functional targets are provided for use in methods for diagnosis of illnesses associated with PCDH19 protein deficiency, methods for the identification of a predisposition to such illnesses and methods of screening to identify carriers of such illnesses, and methods and kits for screening candidate agents for potential therapeutic use in the treatment of illnesses associated with PCDH19 protein deficiency.

Although a preferred embodiment of the method of the present invention has been described in the foregoing detailed description, it will be understood that the invention is not limited to the embodiment disclosed, but is capable of numerous rearrangements, modifications and substitutions without departing from the scope of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES

Blanco P, Sargent C A, Boucher C A, Mitchell M, Affara N A. Conservation of PCDHX in mammals; expression of human X/Y genes predominantly in brain. *Mamm Genome* 11, 906-14 (2000).

Lipinski C A, Lombardo F, Dominy B W, Feeney P J. Experimental and computational approaches to estimate solubility and permeability in drug discovery and development settings. *Adv Drug Del Rev* 46, 3-26 (2001).

Fabisiak K, Erickson R P. A familial form of convulsive disorder with or without mental retardation limited to females: extension of a pedigree limits possible genetic mechanisms. *Cli. Genet* 38, 353-358 (1990).

Gaitan Y, Bouchard M. Expression of the δ-protocadherin gene Pcdh19 in the developing mouse embryo. *Gene Express Patterns* 6, 893-899 (2006).

Juberg R C, Hellman C D. A new familial form of convulsive disorder and mental retardation limited to females. *J Pediatr* 79, 726-732 (1971).

Kim S Y et al. Spatiotemporal expression pattern of non-clustered protocadherin family members in the developing rat brain. *Neuroscience* 147, 996-1021 (2007).

Lambson B, Affara N A, Mitchell M, Ferguson-Smith M A. Evolution of DNA sequence homologies between the sex chromosomes in primate species. *Genomics* 14, 1032-40 (1992).

Maquat L E. Nonsense-mediated mRNA decay: splicing, translation and mRNP dynamics. *Nature Rev Mol. Cell Biol* 5, 89-99 (2004).

McKee S. X-linked epilepsy affecting females and sparing males: report of a second family. *J Med Genet* 43, Suppl 1, S48 (2006).

Morishita H. et al. Structure of the cadherin-related neuronal receptor/protocadherin-alpha first extracellular cadherin domain reveals diversity across cadherin families. *J Biol Chem* 281, 33650-33663 (2006).

Page D C, Harper M E, Love J, Botstein D. Occurrence of a transposition from the X-chromosome long arm to the Y-chromosome short arm during human evolution. *Nature* 311, 119-123 (1984).

Patel S D et al. Type II cadherin ectodomain structures: implications for classical cadherin specificity. *Cell* 124, 1255-1268 (2006).

Redies C, Vanhalst K, van Roy F. Protocadherins: unique structures and functions. *Cell Mol Life Sci* 62, 2840-2852 (2005).

Ryan S G, Chance P F, Zou C H, Spinner N B, Golden J A, Smietana S. Epilepsy and mental retardation limited to females: an X-linked dominant disorder with male sparing. *Nature Genet* 17, 92-95 (1997).

Sambrook, J., Fritsch, E. F., and Maniatis, T., in *Molecular Cloning: A Laboratory Manual*. Cold Spring Harbor Laboratory Press, NY, Vol 1, 2, 3 (1989).

Saviozzi S, Cordero F, Lo Iacono M, Novello S, Scagliotti G V, Calogero R A. Selection of suitable reference genes for accurate normalization of gene expression profile studies in non-small cell lung cancer. *BMC Cancer* 6, 200 (2006).

Scheffer I E, Harkin L A, Grinton B E, Dibbens L M, Turner S J, Zielinski M A, Xu R, Jackson G, Adams J, Connellan M, Petrou S, Wellard R M, Briellmann R S, Wallace R H, Mulley J C, Berkovic S F. Temporal lobe epilepsy and GEFS+ phenotypes associated with SCN1B mutations. *Brain* 130, 100-109 (2007).

Scheffer I E, Turner S J, Turelli L, Haan E, Mazarib A, Neufeld M Y, Korczyn A D, Mulley J C, Berkovic S F. Epilepsy and mental retardation limited to females (EFMR): Underrecognition of a remarkable phenotype and confirmation of linkage. *EPILEPSIA* 45 (Suppl 7), 226 (2004).

Vanhalst K, Kools P, Staes K, van Roy F, Redies C. Proto-cadherins: a gene family expressed differentially in the mouse brain. *Cell Mol Life Sci* 62, 1247-1259 (2005).

Wilson L D, Ross S A, Lepore D A, Wada T, Penninger J M, Thomas P Q. Developmentally regulated expression of the regulator of G-protein signaling gene 2 (Rgs2) in the embryonic mouse pituitary. *Gene Expression Patterns* 5, 305-311 (2005).

Wu Q, Maniatis T. A striking organization of a large family of human neural cadherin-like cell adhesion genes. *Cell* 97, 779-790 (1999).

Yagi T, Takeichi M. Cadherin superfamily genes: functions, genomic organization, and neurologic diversity. *Genes Dev* 14, 1169-1180 (2000).

---

The invention claimed is:

1. A protocadherin 19 (PCDH19) mutation-specific oligonucleotide consisting of 20 to 50 contiguous nucleotides of a mutant nucleotide sequence of SEQ ID NO: 1, wherein the 20 to 50 contiguous nucleotides of the mutant nucleotide sequence of SEQ ID NO: 1 consist of one or more PCDH19 mutations selected from the group consisting of 1322T>A, 253C>T, 2012C>G, 2030_2031insT, 1671C>G, and 1091_1092insC relative to SEQ ID NO: 1, and wherein the oligonucleotide is detectably labeled.

2. A protocadherin 19 (PCDH19) mutation-specific oligonucleotide consisting of 20 to 30 contiguous nucleotides of a mutant nucleotide sequence of SEQ ID NO: 1, wherein the 20 to 30 contiguous nucleotides of the mutant nucleotide sequence of SEQ ID NO: 1 consist of one or more PCDH19 mutations selected from the group consisting of 1322T>A, 253C>T, 2012C>G, 2030_2031insT, 1671C>G, and 1091_1092insC relative to SEQ ID NO: 1, and wherein the oligonucleotide is detectably labeled.

3. A kit for diagnosing an illness related to PCDH19 function, comprising the PCDH19 mutation-specific oligonucleotide of claim 1, and instructions for the operation of a method for diagnosing an illness related to PCDH19 function.

4. The PCDH19 mutation-specific oligonucleotide of claim 1, wherein the oligonucleotide consists of 30 to 50 contiguous nucleotides.

* * * * *

SEQUENCE LISTING

```
<160> NUMBER OF SEQ ID NOS: 41

<210> SEQ ID NO 1
<211> LENGTH: 3447
<212> TYPE: DNA
<213> ORGANISM: Homo sapiens

<400> SEQUENCE: 1
atggagtcgc tcctgctgcc ggtgctgctg ctgctggcca tactgtggac gcaggctgcc      60
gccctcatta atctcaagta ctcggtagaa gaggagcagc gcgccgggac ggtgattgcc     120
aacgtggcca agacgcgcg agaggcgggc ttcgcgctgg accccggca ggcttcagcc      180 tttcgcgtgg tgtccaactc ggctccacac ctagtggaca tcaatcccag ctctggcctg     240
ctggtcacca agcagaagat tgaccgtgat ctgctgtgcc gccagagccc caagtgcatc     300
atctcgctcg aggtcatgtc cagctcaatg gaaatctgcg tgataaaggt ggagatcaag     360
gacctgaacg acaatgcgcc cagtttcccg gcagcacaga tcgagctgga gatctcggag     420
gcagccagcc ctggcacgcg catcccgctg gacagcgctt acgatccaga ctcaggaagc     480
tttggcgtgc agacttacga gctcacgccc aacgagctgt tcggcctgga gatcaagacg     540
cgcggcgacg gctcccgctt tgccgaactc gtggtggaaa agagcctgga ccgcgagacg     600
cagtcgcact acagcttccg aatcactgcg ctagacggtg gcgacccgcc gcgcctgggc     660
accgttggcc ttagtatcaa ggtgaccgac tccaatgaca caaccccggt gtttagcgag     720
tccacctacg cggtgagcgt gccagaaaac tcgcctccca acacacccgt catccgcctc     780
aacgccagcg atccagacga gggcaccaac ggccaggtgg tctactcctt ctatggctac    840
```

```
gtcaacgacc gcacgcgcga gctctttcag atcgacccgc acagtggcct ggtcactgtc    900
actggcgctt tagactacga agaggggcac gtgtacgaac tggacgtgca ggctaaggac    960
ttggggccca attccatccc ggcacactgc aaggtcaccg tcagcgtgct ggacaccaat   1020
gacaatccgc cggtcatcaa cctgctgtca gtcaacagtg agcttgtgga ggtcagcgag   1080
agcgccccc cgggctacgt gatcgccttg gtgcgggtgt ctgatcgcga ctcaggcctc   1140
aatgacgtg tgcagtgccg tttgctgggc aatgtgccct ttcgactgca ggaatatgag   1200
agcttctcca ctattctggt ggacggacgg ctggaccgcg agcagcacga ccaatacaac   1260
ctcacaattc aggcacgcga cggcggcgtg cccatgctgc agagtgccaa gtcctttacc   1320
gtgctcatca ctgacgaaaa tgacaaccac ccgcactttt ccaagcccta ctaccaggtc   1380
attgtgcagg agaacaacac gcctggcgcc tatctgctct ctgtgtctgc tcgcgacccc   1440
gacctgggtc tcaacggcag tgtctcctac cagatcgtgc cgtcgcaggt gcgggacatg   1500
cctgtcttca cctatgtctc catcaatccc aactcaggcg acatctacgc gctgcgatcc   1560
tttaaccacg agcagaccaa ggcgttcgaa ttcaaggtgc tggccaagga cggcggcctt   1620
ccctcactgc aaagcaacgc tacggtgcgg gtcatcatcc tcgacgtcaa cgacaacacc   1680
ccggtcatca cagccccacc tctgattaac ggcactgccg aggtctacat accccgcaac   1740
tctggcatag ctacctggt gactgttgtc aaggcagaag actacgatga gggcgaaaat   1800
ggccgagtca cctacgacat gaccgagggc gaccgcggct tctttgaaat agaccaggtc   1860
aatggcgaag tcagaaccac ccgcaccttc ggggagagct ccaagtcctc ctatgagctt   1920
atcgtggtgg ctcacgacca cggcaagaca tctctctctg cctctgctct cgtcctaatc   1980
tacttgtccc ctgctctcga tgcccaagag tcaatgggct ctgtgaactt gtccttgatt   2040
ttcattattg ccctgggctc cattgcgggc atcctctttg taactatgat cttcgtggca   2100
atcaagtgca agcgagacaa caaagagatc cggacctaca actgcagtaa ttgtttaacc   2160
atcacttgtc tcctcggctg ttttataaaa ggacaaaaca gcaagtgtct gcattgcatc   2220
tcggtttctc ccattagcga ggagcaagac aaaaagacag aggagaaagt gagcctaagg   2280
ggaaagagaa ttgctgagta ctcctatggg catcaaaaga aatcaagcaa gaagaaaaaa   2340
atcagtaaga atgacatccg cctggtaccc cgggatgtgg aggagacaga caagatgaac   2400
gttgtcagtt gctcttccct gacctcctcc ctcaactatt ttgactacca ccagcagacg   2460
ctgccctgg gctgccgccg ctctgagagc actttcctga atgtggagaa ccagaatacc   2520
cgcaacacca gtgctaacca catctaccat cactcttca acagccaggg gccccagcag   2580
cctgacctga ttatcaacgg tgtgcctctg cctgagactg aaaactattc ttttgactcc   2640
aactacgtga atagccgagc ccatttaatc aagagcagct ccaccttcaa ggacttagag   2700
ggcaacagcc tgaaggatag tggacatgag gagagtgacc aaaactgacag tgagcatgat   2760
gtccagcgga gcctgtattg tgatactgct gtcaacgatg tgctgaacac cagtgtgacc   2820
tccatgggat ctcagatgcc tgatcatgat cagaatgaag gatttcattg ccgggaagaa   2880
tgccggattc ttggccactc tgacaggtgc tggatgcccc ggaacccat gcccatccgt   2940
tccaagtccc ctgagcatgt gaggaacatc atcgcgctgt ctattgaagc tactgctgct   3000
gatgtcgagg cttatgacga ctgcggcccc accaaacgga cttcgcaac ctttgggaaa   3060
gatgtcagcg accaccgc tgaggagagg cctaccctga aaggcaagag gactgtcgat   3120
gtgaccatct gcagccccaa ggtcaacagc gttatccggg aggcaggcaa tggctgtgag   3180
```

-continued

```
gcgattagcc ctgtcacctc cccctccac ctcaagagct ctctgcccac caagccttcc    3240
gtgtcttaca ccattgccct ggctccccca gcccgtgatc tggagcagta tgtcaacaat    3300
gtcaacaatg gccctactcg tccctctgaa gctgagcccc gtggagctga tagcgagaaa    3360
gtcatgcatg aggtcagccc cattctgaag gaaggtcgca acaaagagtc cctggtgtg    3420 aagcgtctga aggatatcgt tctctaa                                         3447
```

<210> SEQ ID NO 2
<211> LENGTH: 1148
<212> TYPE: PRT
<213> ORGANISM: Homo sapiens

<400> SEQUENCE: 2

```
Met Glu Ser Leu Leu Pro Val Leu Leu Leu Ala Ile Leu Trp
1               5                   10                  15

Thr Gln Ala Ala Ala Leu Ile Asn Leu Lys Tyr Ser Val Glu Glu
                20                  25                  30

Gln Arg Ala Gly Thr Val Ile Ala Asn Val Ala Lys Asp Ala Arg Glu
            35                  40                  45

Ala Gly Phe Ala Leu Asp Pro Arg Gln Ala Ser Ala Phe Arg Val Val
        50                  55                  60

Ser Asn Ser Ala Pro His Leu Val Asp Ile Asn Pro Ser Ser Gly Leu
65                  70                  75                  80

Leu Val Thr Lys Gln Lys Ile Asp Arg Asp Leu Leu Cys Arg Gln Ser
                85                  90                  95

Pro Lys Cys Ile Ile Ser Leu Glu Val Met Ser Ser Met Glu Ile
            100                 105                 110

Cys Val Ile Lys Val Glu Ile Lys Asp Leu Asn Asp Asn Ala Pro Ser
        115                 120                 125

Phe Pro Ala Ala Gln Ile Glu Leu Glu Ile Ser Glu Ala Ala Ser Pro
130                 135                 140

Gly Thr Arg Ile Pro Leu Asp Ser Ala Tyr Asp Pro Asp Ser Gly Ser
145                 150                 155                 160

Phe Gly Val Gln Thr Tyr Glu Leu Thr Pro Asn Glu Leu Phe Gly Leu
                165                 170                 175

Glu Ile Lys Thr Arg Gly Asp Gly Ser Arg Phe Ala Glu Leu Val Val
            180                 185                 190

Glu Lys Ser Leu Asp Arg Glu Thr Gln Ser His Tyr Ser Phe Arg Ile
        195                 200                 205

Thr Ala Leu Asp Gly Gly Asp Pro Pro Arg Leu Gly Thr Val Gly Leu
    210                 215                 220

Ser Ile Lys Val Thr Asp Ser Asn Asp Asn Pro Val Phe Ser Glu
225                 230                 235                 240

Ser Thr Tyr Ala Val Ser Val Pro Glu Asn Ser Pro Asn Thr Pro
                245                 250                 255

Val Ile Arg Leu Asn Ala Ser Asp Pro Asp Glu Gly Thr Asn Gly Gln
            260                 265                 270

Val Val Tyr Ser Phe Tyr Gly Tyr Val Asn Asp Arg Thr Arg Glu Leu
        275                 280                 285

Phe Gln Ile Asp Pro His Ser Gly Leu Val Thr Val Thr Gly Ala Leu
    290                 295                 300

Asp Tyr Glu Glu Gly His Val Tyr Glu Leu Asp Val Gln Ala Lys Asp
305                 310                 315                 320

Leu Gly Pro Asn Ser Ile Pro Ala His Cys Lys Val Thr Val Ser Val
```

```
                325                 330                 335
Leu Asp Thr Asn Asp Asn Pro Pro Val Ile Asn Leu Leu Ser Val Asn
            340                 345                 350
Ser Glu Leu Val Glu Val Ser Glu Ser Ala Pro Pro Gly Tyr Val Ile
            355                 360                 365
Ala Leu Val Arg Val Ser Asp Arg Asp Ser Gly Leu Asn Gly Arg Val
            370                 375                 380
Gln Cys Arg Leu Leu Gly Asn Val Pro Phe Arg Leu Gln Glu Tyr Glu
385                 390                 395                 400
Ser Phe Ser Thr Ile Leu Val Asp Gly Arg Leu Asp Arg Glu Gln His
            405                 410                 415
Asp Gln Tyr Asn Leu Thr Ile Gln Ala Arg Asp Gly Gly Val Pro Met
            420                 425                 430
Leu Gln Ser Ala Lys Ser Phe Thr Val Leu Ile Thr Asp Glu Asn Asp
            435                 440                 445
Asn His Pro His Phe Ser Lys Pro Tyr Tyr Gln Val Ile Val Gln Glu
            450                 455                 460
Asn Asn Thr Pro Gly Ala Tyr Leu Leu Ser Val Ser Ala Arg Asp Pro
465                 470                 475                 480
Asp Leu Gly Leu Asn Gly Ser Val Ser Tyr Gln Ile Val Pro Ser Gln
            485                 490                 495
Val Arg Asp Met Pro Val Phe Thr Tyr Val Ser Ile Asn Pro Asn Ser
            500                 505                 510
Gly Asp Ile Tyr Ala Leu Arg Ser Phe Asn His Glu Gln Thr Lys Ala
            515                 520                 525
Phe Glu Phe Lys Val Leu Ala Lys Asp Gly Gly Leu Pro Ser Leu Gln
            530                 535                 540
Ser Asn Ala Thr Val Arg Val Ile Ile Leu Asp Val Asn Asp Asn Thr
545                 550                 555                 560
Pro Val Ile Thr Ala Pro Pro Leu Ile Asn Gly Thr Ala Glu Val Tyr
            565                 570                 575
Ile Pro Arg Asn Ser Gly Ile Gly Tyr Leu Val Thr Val Lys Ala
            580                 585                 590
Glu Asp Tyr Asp Glu Gly Glu Asn Gly Arg Val Thr Tyr Asp Met Thr
            595                 600                 605
Glu Gly Asp Arg Gly Phe Phe Glu Ile Asp Gln Val Asn Gly Glu Val
            610                 615                 620
Arg Thr Thr Arg Thr Phe Gly Glu Ser Ser Lys Ser Ser Tyr Glu Leu
625                 630                 635                 640
Ile Val Val Ala His Asp His Gly Lys Thr Ser Leu Ser Ala Ser Ala
            645                 650                 655
Leu Val Leu Ile Tyr Leu Ser Pro Ala Leu Asp Ala Gln Glu Ser Met
            660                 665                 670
Gly Ser Val Asn Leu Ser Leu Ile Phe Ile Ile Ala Leu Gly Ser Ile
            675                 680                 685
Ala Gly Ile Leu Phe Val Thr Met Ile Phe Val Ala Ile Lys Cys Lys
            690                 695                 700
Arg Asp Asn Lys Glu Ile Arg Thr Tyr Asn Cys Ser Asn Cys Leu Thr
705                 710                 715                 720
Ile Thr Cys Leu Leu Gly Cys Phe Ile Lys Gly Gln Asn Ser Lys Cys
            725                 730                 735
Leu His Cys Ile Ser Val Ser Pro Ile Ser Glu Glu Gln Asp Lys Lys
            740                 745                 750
```

```
Thr Glu Glu Lys Val Ser Leu Arg Gly Lys Arg Ile Ala Glu Tyr Ser
        755                 760                 765

Tyr Gly His Gln Lys Lys Ser Ser Lys Lys Lys Ile Ser Lys Asn
    770                 775                 780

Asp Ile Arg Leu Val Pro Arg Asp Val Glu Thr Asp Lys Met Asn
785                 790                 795                 800

Val Val Ser Cys Ser Ser Leu Thr Ser Ser Leu Asn Tyr Phe Asp Tyr
                805                 810                 815

His Gln Gln Thr Leu Pro Leu Gly Cys Arg Arg Ser Glu Ser Thr Phe
            820                 825                 830

Leu Asn Val Glu Asn Gln Asn Thr Arg Asn Thr Ser Ala Asn His Ile
                835                 840                 845

Tyr His His Ser Phe Asn Ser Gln Gly Pro Gln Gln Pro Asp Leu Ile
            850                 855                 860

Ile Asn Gly Val Pro Leu Pro Glu Thr Glu Asn Tyr Ser Phe Asp Ser
865                 870                 875                 880

Asn Tyr Val Asn Ser Arg Ala His Leu Ile Lys Ser Ser Thr Phe
                885                 890                 895

Lys Asp Leu Glu Gly Asn Ser Leu Lys Asp Ser Gly His Glu Glu Ser
            900                 905                 910

Asp Gln Thr Asp Ser Glu His Asp Val Gln Arg Ser Leu Tyr Cys Asp
            915                 920                 925

Thr Ala Val Asn Asp Val Leu Asn Thr Ser Val Thr Ser Met Gly Ser
    930                 935                 940

Gln Met Pro Asp His Asp Gln Asn Glu Gly Phe His Cys Arg Glu Glu
945                 950                 955                 960

Cys Arg Ile Leu Gly His Ser Asp Arg Cys Trp Met Pro Arg Asn Pro
                965                 970                 975

Met Pro Ile Arg Ser Lys Ser Pro Glu His Val Arg Asn Ile Ile Ala
            980                 985                 990

Leu Ser Ile Glu Ala Thr Ala Ala  Asp Val Glu Ala Tyr  Asp Asp Cys
        995                 1000                1005

Gly Pro  Thr Lys Arg Thr Phe  Ala Thr Phe Gly Lys  Asp Val Ser
    1010                1015                1020

Asp His  Pro Ala Glu Glu Arg  Pro Thr Leu Lys Gly  Lys Arg Thr
    1025                1030                1035

Val Asp  Val Thr Ile Cys Ser  Pro Lys Val Asn Ser  Val Ile Arg
    1040                1045                1050

Glu Ala  Gly Asn Gly Cys Glu  Ala Ile Ser Pro Val  Thr Ser Pro
    1055                1060                1065

Leu His  Leu Lys Ser Ser Leu  Pro Thr Lys Pro Ser  Val Ser Tyr
    1070                1075                1080

Thr Ile  Ala Leu Ala Pro Pro  Ala Arg Asp Leu Glu  Gln Tyr Val
    1085                1090                1095

Asn Asn  Val Asn Asn Gly Pro  Thr Arg Pro Ser Glu  Ala Glu Pro
    1100                1105                1110

Arg Gly  Ala Asp Ser Glu Lys  Val Met His Glu Val  Ser Pro Ile
    1115                1120                1125

Leu Lys  Glu Gly Arg Asn Lys  Glu Ser Pro Gly Val  Lys Arg Leu
    1130                1135                1140

Lys Asp  Ile Val Leu
    1145
```

```
<210> SEQ ID NO 3
<211> LENGTH: 22
<212> TYPE: DNA
<213> ORGANISM: Homo sapiens

<400> SEQUENCE: 3
ccggattctt ggccactctg ac                                           22

<210> SEQ ID NO 4
<211> LENGTH: 21
<212> TYPE: DNA
<213> ORGANISM: Homo sapiens

<400> SEQUENCE: 4
caatggtgta agacacggaa g                                            21

<210> SEQ ID NO 5
<211> LENGTH: 25
<212> TYPE: DNA
<213> ORGANISM: Homo sapiens

<400> SEQUENCE: 5
gtaacaagtg tacctggtat ggact                                        25

<210> SEQ ID NO 6
<211> LENGTH: 21
<212> TYPE: DNA
<213> ORGANISM: Homo sapiens

<400> SEQUENCE: 6 tcaacctttha ctttcatcac g                                           21

<210> SEQ ID NO 7
<211> LENGTH: 24
<212> TYPE: DNA
<213> ORGANISM: Homo sapiens

<400> SEQUENCE: 7
tacaacaaac tgtcacaagt gttt                                         24

<210> SEQ ID NO 8
<211> LENGTH: 21
<212> TYPE: DNA
<213> ORGANISM: Homo sapiens

<400> SEQUENCE: 8 tcaacctttha ctttcatcac a                                           21

<210> SEQ ID NO 9
<211> LENGTH: 20
<212> TYPE: DNA
<213> ORGANISM: Homo sapiens

<400> SEQUENCE: 9
aaccagaata cccgcaacac                                              20

<210> SEQ ID NO 10
<211> LENGTH: 20
<212> TYPE: DNA
<213> ORGANISM: Homo sapiens

<400> SEQUENCE: 10
ctgcagatgg tcacatcgac                                              20
```

```
<210> SEQ ID NO 11
<211> LENGTH: 20
<212> TYPE: PRT
<213> ORGANISM: Homo sapiens

<400> SEQUENCE: 11

Met Leu Gln Ser Ala Lys Ser Phe Thr Val Leu Ile Thr Asp Glu Asn
1               5                   10                  15

Asp Asn His Pro
            20

<210> SEQ ID NO 12
<211> LENGTH: 20
<212> TYPE: PRT
<213> ORGANISM: Homo sapiens

<400> SEQUENCE: 12

Pro Leu Asn Ser Thr Lys Ser Phe Ala Ile Lys Ile Leu Asp Glu Asn
1               5                   10                  15

Asp Asn Pro Pro
            20

<210> SEQ ID NO 13
<211> LENGTH: 20
<212> TYPE: PRT
<213> ORGANISM: Homo sapiens

<400> SEQUENCE: 13

Ala Leu Ser Thr Ser Lys Ser Ile Gln Val Gln Val Ser Asp Val Asn
1               5                   10                  15

Asp Asn Ala Pro
            20

<210> SEQ ID NO 14
<211> LENGTH: 20
<212> TYPE: PRT
<213> ORGANISM: Homo sapiens

<400> SEQUENCE: 14

Ser Leu Ser Thr Val Lys His Phe Thr Val Gln Ile Asn Asp Ile Asn
1               5                   10                  15

Asp Asn Pro Pro
            20

<210> SEQ ID NO 15
<211> LENGTH: 20
<212> TYPE: PRT
<213> ORGANISM: Homo sapiens

<400> SEQUENCE: 15

Pro Leu Arg Thr Val Arg Pro Tyr Thr Val Arg Val Gly Asp Glu Asn
1               5                   10                  15

Asp Asn Ala Pro
            20

<210> SEQ ID NO 16
<211> LENGTH: 20
<212> TYPE: PRT
<213> ORGANISM: Homo sapiens

<400> SEQUENCE: 16
```

```
Pro Leu Gln Ser Gln Ala Ala Val Ile Val Thr Val Leu Asp Glu Asn
1               5                   10                  15

Asp Asn Ser Pro
            20

<210> SEQ ID NO 17
<211> LENGTH: 20
<212> TYPE: PRT
<213> ORGANISM: Homo sapiens

<400> SEQUENCE: 17

Pro Arg Ser Ser Gln Ala Ile Leu Arg Val Leu Ile Thr Asp Val Asn
1               5                   10                  15

Asp Asn Ser Pro
            20

<210> SEQ ID NO 18
<211> LENGTH: 20
<212> TYPE: PRT
<213> ORGANISM: Homo sapiens

<400> SEQUENCE: 18

Ser Leu Trp Ala Thr Ala Ser Val Ser Val Glu Val Ala Asp Val Asn
1               5                   10                  15

Asp Asn Ala Pro
            20

<210> SEQ ID NO 19
<211> LENGTH: 20
<212> TYPE: PRT
<213> ORGANISM: Homo sapiens

<400> SEQUENCE: 19

Pro Leu Ser Ser Thr Ala Gln Ile His Val Leu Val Thr Asp Ala Asn
1               5                   10                  15

Asp Asn Ala Pro
            20

<210> SEQ ID NO 20
<211> LENGTH: 20
<212> TYPE: PRT
<213> ORGANISM: Homo sapiens

<400> SEQUENCE: 20

Arg Leu Lys Thr Glu Gln Ser Ile Thr Val Leu Val Ser Asp Val Asn
1               5                   10                  15

Asp Asn Ala Pro
            20

<210> SEQ ID NO 21
<211> LENGTH: 20
<212> TYPE: PRT
<213> ORGANISM: Homo sapiens

<400> SEQUENCE: 21

Met Leu Gln Ser Ala Lys Ser Phe Thr Val Arg Ile Thr Asp Glu Asn
1               5                   10                  15

Asp Asn His Pro
            20

<210> SEQ ID NO 22
<211> LENGTH: 20
```

```
<212> TYPE: PRT
<213> ORGANISM: Homo sapiens

<400> SEQUENCE: 22

Met Leu Gln Ser Ala Lys Ser Phe Thr Val Arg Ile Thr Asp Glu Asn
1               5                   10                  15

Asp Asn His Pro
            20

<210> SEQ ID NO 23
<211> LENGTH: 20
<212> TYPE: PRT
<213> ORGANISM: Homo sapiens

<400> SEQUENCE: 23

Ser Leu Gln Ala Thr Lys Ser Phe Thr Val Lys Ile Thr Asp Glu Asn
1               5                   10                  15

Asp Asn His Pro
            20

<210> SEQ ID NO 24
<211> LENGTH: 20
<212> TYPE: PRT
<213> ORGANISM: Homo sapiens

<400> SEQUENCE: 24

Pro Leu Arg Ser Ser Lys Ser Phe Ala Val Lys Val Thr Asp Glu Asn
1               5                   10                  15

Asp Asn Pro Pro
            20

<210> SEQ ID NO 25
<211> LENGTH: 20
<212> TYPE: PRT
<213> ORGANISM: Homo sapiens

<400> SEQUENCE: 25

Ala Thr Val Arg Val Ile Ile Leu Asp Val Asn Asp Asn Thr Pro Val
1               5                   10                  15

Ile Thr Ala Pro
            20

<210> SEQ ID NO 26
<211> LENGTH: 20
<212> TYPE: PRT
<213> ORGANISM: Homo sapiens

<400> SEQUENCE: 26

Lys Ser Phe Ala Ile Lys Ile Leu Asp Glu Asn Asp Asn Pro Pro Arg
1               5                   10                  15

Phe Thr Lys Gly
            20

<210> SEQ ID NO 27
<211> LENGTH: 20
<212> TYPE: PRT
<213> ORGANISM: Homo sapiens

<400> SEQUENCE: 27

Lys Ser Ile Gln Val Gln Val Ser Asp Val Asn Asp Asn Ala Pro Arg
1               5                   10                  15

Phe Ser Gln Pro
```

20

<210> SEQ ID NO 28
<211> LENGTH: 20
<212> TYPE: PRT
<213> ORGANISM: Homo sapiens

<400> SEQUENCE: 28

Lys His Phe Thr Val Gln Ile Asn Asp Ile Asn Asp Asn Pro Pro His
1               5                   10                  15

Phe Gln Arg Ser
            20

<210> SEQ ID NO 29
<211> LENGTH: 20
<212> TYPE: PRT
<213> ORGANISM: Homo sapiens

<400> SEQUENCE: 29

Arg Pro Tyr Thr Val Arg Val Gly Asp Glu Asn Asp Asn Ala Pro Leu
1               5                   10                  15

Phe Thr Arg Pro
            20

<210> SEQ ID NO 30
<211> LENGTH: 20
<212> TYPE: PRT
<213> ORGANISM: Homo sapiens

<400> SEQUENCE: 30

Ala Ala Val Ile Val Thr Val Leu Asp Glu Asn Asp Asn Ser Pro Lys
1               5                   10                  15

Phe Thr His Asn
            20

<210> SEQ ID NO 31
<211> LENGTH: 20
<212> TYPE: PRT
<213> ORGANISM: Homo sapiens

<400> SEQUENCE: 31

Ala Ile Leu Arg Val Leu Ile Thr Asp Val Asn Asp Asn Ser Pro Arg
1               5                   10                  15

Phe Glu Lys Ser
            20

<210> SEQ ID NO 32
<211> LENGTH: 20
<212> TYPE: PRT
<213> ORGANISM: Homo sapiens

<400> SEQUENCE: 32

Ala Ser Val Ser Val Glu Val Ala Asp Val Asn Asp Asn Ala Pro Ala
1               5                   10                  15

Phe Ala Gln Pro
            20

<210> SEQ ID NO 33
<211> LENGTH: 20
<212> TYPE: PRT
<213> ORGANISM: Homo sapiens

<400> SEQUENCE: 33

-continued

Ala Gln Ile His Val Leu Val Thr Asp Ala Asn Asp Asn Ala Pro Val
1               5                   10                  15

Phe Ser Gln Asp
            20

<210> SEQ ID NO 34
<211> LENGTH: 20
<212> TYPE: PRT
<213> ORGANISM: Homo sapiens

<400> SEQUENCE: 34

Ala Leu Val Arg Val Leu Val Leu Asp Ala Asn Asp Asn Ser Pro Phe
1               5                   10                  15

Val Leu Tyr Pro
            20

<210> SEQ ID NO 35
<211> LENGTH: 20
<212> TYPE: PRT
<213> ORGANISM: Homo sapiens

<400> SEQUENCE: 35

Ala Thr Val Arg Val Ile Ile Leu Asp Val Asn Asp Asn Thr Pro Val
1               5                   10                  15

Ile Thr Ala Pro
            20

<210> SEQ ID NO 36
<211> LENGTH: 20
<212> TYPE: PRT
<213> ORGANISM: Homo sapiens

<400> SEQUENCE: 36

Ala Thr Val Arg Val Ile Ile Leu Asp Val Asn Asp Asn Thr Pro Val
1               5                   10                  15

Ile Thr Ala Pro
            20

<210> SEQ ID NO 37
<211> LENGTH: 20
<212> TYPE: PRT
<213> ORGANISM: Homo sapiens

<400> SEQUENCE: 37

Ala Thr Val Arg Val Ile Val Leu Asp Val Asn Asp Asn Thr Pro Val
1               5                   10                  15

Ile Thr Ala Pro
            20

<210> SEQ ID NO 38
<211> LENGTH: 20
<212> TYPE: PRT
<213> ORGANISM: Homo sapiens

<400> SEQUENCE: 38

Ala Thr Val Arg Ile Val Val Leu Asp Val Asn Asp Asn Thr Pro Val
1               5                   10                  15

Met Thr Thr Pro
            20

<210> SEQ ID NO 39

```
<211> LENGTH: 13
<212> TYPE: DNA
<213> ORGANISM: Homo sapiens

<400> SEQUENCE: 39
accaagyaga aga                                                        13

<210> SEQ ID NO 40
<211> LENGTH: 13
<212> TYPE: DNA
<213> ORGANISM: Homo sapiens

<400> SEQUENCE: 40
accaagcaga aga                                                        13

<210> SEQ ID NO 41
<211> LENGTH: 13
<212> TYPE: DNA
<213> ORGANISM: Homo sapiens

<400> SEQUENCE: 41
accaagyaga aga                                                        13
```